(12) United States Patent
Gouda et al.

(10) Patent No.: US 8,980,040 B2
(45) Date of Patent: Mar. 17, 2015

(54) MANUFACTURING METHOD OF ABSORBENT ARTICLE

(75) Inventors: Hidefumi Gouda, Kanonji (JP); Hirotomo Mukai, Kanonji (JP)

(73) Assignee: Unicharm Corporation, Ehime (JP)

(*) Notice: Subject to any disclaimer, the term of this patent is extended or adjusted under 35 U.S.C. 154(b) by 311 days.

(21) Appl. No.: 13/576,031

(22) PCT Filed: Dec. 28, 2010

(86) PCT No.: PCT/JP2010/073896
§ 371 (c)(1),
(2), (4) Date: Jul. 30, 2012

(87) PCT Pub. No.: WO2011/093001
PCT Pub. Date: Aug. 4, 2011

(65) Prior Publication Data
US 2012/0302417 A1     Nov. 29, 2012

(30) Foreign Application Priority Data

Jan. 29, 2010 (JP) .................................. 2010-019807

(51) Int. Cl.
*A61F 13/15* (2006.01)
(52) U.S. Cl.
CPC ..... *A61F 13/15804* (2013.01); *A61F 13/15699* (2013.01); *A61F 13/15593* (2013.01)
USPC ....................................................... 156/267
(58) Field of Classification Search
USPC ....................................................... 156/267
See application file for complete search history.

(56) References Cited

U.S. PATENT DOCUMENTS

| 2004/0040642 A1 | 3/2004 | Otsubo et al. |
| 2004/0108054 A1 | 6/2004 | Otsubo et al. |

(Continued)

FOREIGN PATENT DOCUMENTS

| JP | 11-107007 A | 4/1999 |
| JP | 2001-29389 A | 2/2001 |

(Continued)

OTHER PUBLICATIONS

International Search Report from corresponding PCT application No. PCT/JP2010/073896 dated Apr. 12, 2011 (4 pgs).

(Continued)

*Primary Examiner* — Barbara J Musser
(74) *Attorney, Agent, or Firm* — Brinks Gilson & Lione

(57) ABSTRACT

A method of manufacturing an underpants-type absorbent article having an outer body provided with a mutually separate front piece, back piece and connecting sheet, and wherein the front piece and the back piece are mutually joined at side areas and are mutually connected by the connecting sheet extending in the front-to-rear direction at the crotch area, and an inner body containing an absorptive body and which is overlapped and anchored to the connecting sheet on the inside of the outer body, comprises, in turn, transporting a continuous body of the front piece in the form of a front piece web and a continuous body of the back piece in the form of a back piece web in a machine direction while maintaining a spacing area in a cross-machine direction, forming a continuous body of the outer body in the form of an outer body web by attaching the connecting sheet to the front piece web and the back piece web at intervals in the machine direction so as to straddle the spacing area, cutting the outer body web in order to form edges that define leg holes, and attaching the inner body to the outer body web.

7 Claims, 20 Drawing Sheets

(56) References Cited

U.S. PATENT DOCUMENTS

| | | |
|---|---|---|
| 2009/0326503 A1 | 12/2009 | Lakso et al. |
| 2010/0252178 A1* | 10/2010 | Takino et al. ............ 156/164 |
| 2011/0094661 A1* | 4/2011 | Thorson ............ 156/211 |

FOREIGN PATENT DOCUMENTS

| | | |
|---|---|---|
| JP | 2003-339768 A | 12/2003 |
| JP | 2003-339769 A | 12/2003 |
| JP | 3599722 B | 12/2004 |
| JP | 3732459 B | 10/2005 |
| JP | 2006-55360 A | 3/2006 |
| JP | 2008-194160 A | 8/2008 |
| JP | 2008-228760 A | 10/2008 |
| JP | 2009-536865 A | 10/2009 |

OTHER PUBLICATIONS

Japanese Office Action from corresponding Japanese application No. 2010-019807 dated Jul. 16, 2013 (3 pgs).

* cited by examiner

Fig.5

MANUFACTURING METHOD OF ABSORBENT ARTICLE

RELATED APPLICATION

This application is a 35 U.S.C. §371 national phase filing of International Patent Application No. PCT/JP2010/073896, filed Dec. 28, 2010, through which and to which priority is claimed under 35 U.S.C. §119 to Japanese Patent Application No. 2010-019807, filed Jan. 29, 2010.

TECHNICAL FIELD

The present invention relates to a manufacturing method of an absorbent article.

BACKGROUND ART

A method is known in the prior art of manufacturing an underpants-type absorbent article, which is provided with an outer body, which is provided with a mutually separate front piece, back piece and connecting sheet, and wherein the front piece and the back piece are mutually joined at side areas and mutually connected by the connecting sheet extending in the front-to-rear direction at the crotch area, and an inner body containing an absorptive body and which is overlapped and anchored to the connecting sheet on the inside of the outer body, including: a transport step for transporting a continuous body of the front piece in the form of a front piece web and a continuous body of the back piece in the form of a back piece web in a machine direction while maintaining a spacing area in a cross-machine direction perpendicular to the machine direction, an outer body web forming step for forming a continuous body of the outer body in the form of an outer body web by attaching the connecting sheet to the front piece web and the back piece web at intervals in the machine direction so as to straddle the spacing area, an attachment step for attaching the inner body to the outer body web, and an edge forming step for cutting the outer body web to form edges that define leg holes (see PLT 1). Namely, in this manufacturing method, a portion of the inner body is cut and removed after having attached the inner body to the outer body web.

On the other hand, a method is known in the prior art of manufacturing an absorbent article that is formed from an outer body that integrates a front piece and back piece into a single unit, including: a transport step for transporting a continuous body of the outer body in the form of an outer body web, an edge forming step for cutting the outer body web to form edges that define leg holes, and an attachment step for attaching the inner body to the outer body web (see PLT 2).

CITATION LIST

Patent Literature

PLT 1: Japanese Patent No. 3732459
PLT 2: Japanese Patent No. 3599722

SUMMARY OF INVENTION

Technical Problem

However, in the case of cutting and removing a portion of an inner body in the manner of the manufacturing method of PLT 1, there is the risk of mistakenly cutting and damaging the absorptive body. Namely, there is the risk of damaging the material of the finished product. If the material of the finished product is damaged, the resulting material can no longer be used as a product thereby resulting in the risk of a decrease in productivity of the absorbent article.

With respect to this point, the aforementioned problem may be able to be solved by first cutting an outer body web and then attaching the inner body to the outer body web in the manner of PLT 2.

However, although subsequently described in detail, in a manufacturing method of an absorbent article in which the front piece and back piece are formed from separate sheets, there is the characteristic problem of the risk of product members not being reliably connected. In PLT 2, this characteristic problem does not occur provided the absorbent article is formed from an outer body in which the front piece and back piece are integrated into a single unit.

Namely, even if considering PLT 2, the problem of reliably connecting the product members while simultaneously preventing damage to the material of the finished product cannot be solved.

Solution to Problem

According to the present invention, a manufacturing method of an underpants-type absorbent article is provided, which is provided with an outer body, provided with a mutually separate front piece, back piece and connecting sheet, and wherein the front piece and the back piece are mutually joined at side areas and are mutually connected by the connecting sheet extending in the front-to-rear direction at the crotch area, and an inner body, containing an absorptive body and which is overlapped and anchored to the connecting sheet on the inside of the outer body, comprising, in turn: a transport step for transporting a continuous body of the front piece in the form of a front piece web and a continuous body of the back piece in the form of a back piece web in a machine direction while maintaining a spacing area in a cross-machine direction perpendicular to the machine direction, an outer body web forming step for forming a continuous body of the outer body in the form of an outer body web by attaching the connecting sheet to the front piece web and the back piece web at intervals in the machine direction so as to straddle the spacing area, an edge forming step for cutting the outer body web in order to form edges that define leg holes, and an attachment step for attaching the inner body to the outer body web.

Advantageous Effects of Invention

Product members can be reliably connected while simultaneously preventing damage to the product members.

BRIEF DESCRIPTION OF DRAWINGS

FIG. 5 is a general schematic diagram for explaining a method of manufacturing diapers.

DESCRIPTION OF EMBODIMENTS

The following provides an explanation of the present invention in the case of applying to a disposable underpants-type diaper. Note that the present invention can also be applied to other underpants-type absorbent articles worn in the manner of an undergarment.

Figure 1:
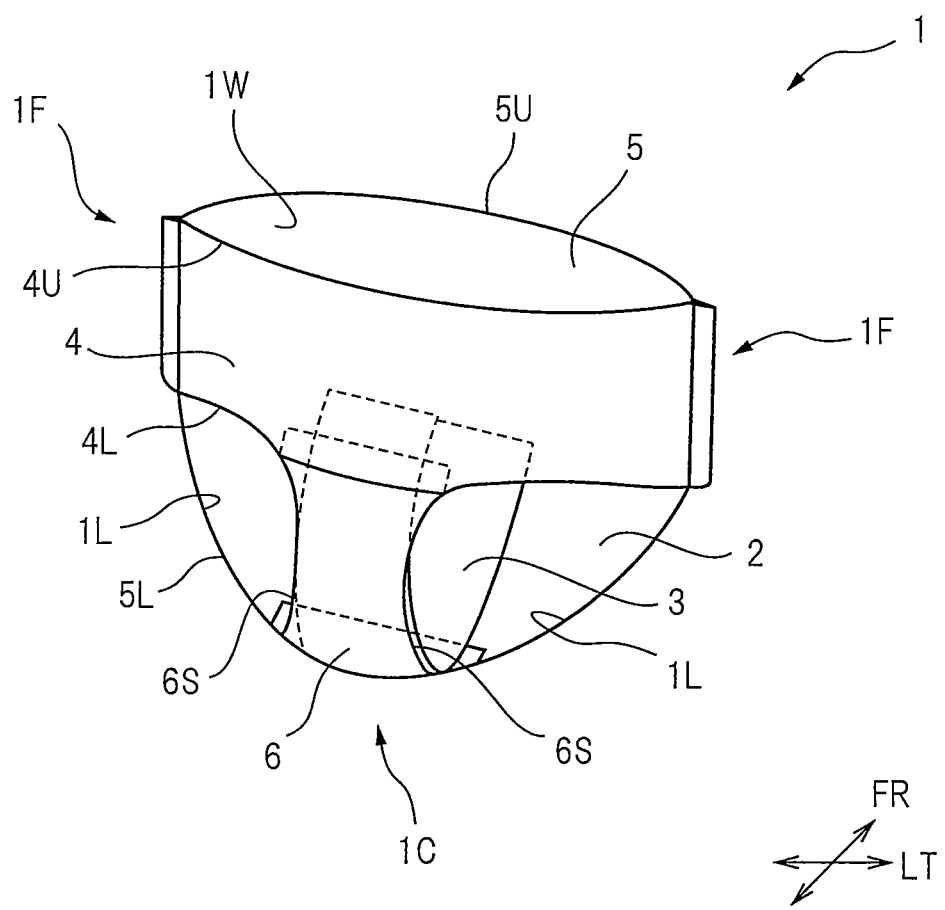
FIG. 1 is a perspective view of a diaper of a first embodiment according to the present invention.

With reference to FIG. 1 showing a first embodiment according to the present invention, a diaper 1 is provided with an outer body 2 and an inner body 3.

The outer body 2 is provided with a mutually separate front piece 4, back piece 5 and connecting sheet 6. In addition to being mutually joined at side areas 1F, the front piece 4 and the back piece 5 are mutually connected by the connecting sheet 6 extending in the front-to-rear direction FR in a crotch area 1C. Here, when worn, the front piece 4 is positioned on the abdominal side of the wearer, and the back piece 5 is positioned on the back side of the wearer. In addition, the diaper 1 is provided with a waist opening or waist hole 1W defined by an upper edge 4U of the front piece 4 and an upper edge 5U of the back piece 5, and a pair of leg openings or leg holes 1L. In this case, each leg hole 1L is defined by an edge 1LE, and this edge 1LE is formed by a lower edge 4L of the front piece 4, a lower edge 5L of the back piece 5, and both edges 6S in the transverse direction LT of the connecting sheet 6. On the other hand, the inner body 3 contains an absorptive body, and is overlapped and anchored to the connecting sheet 6 on the inside of the outer body 2.

Figure 2:
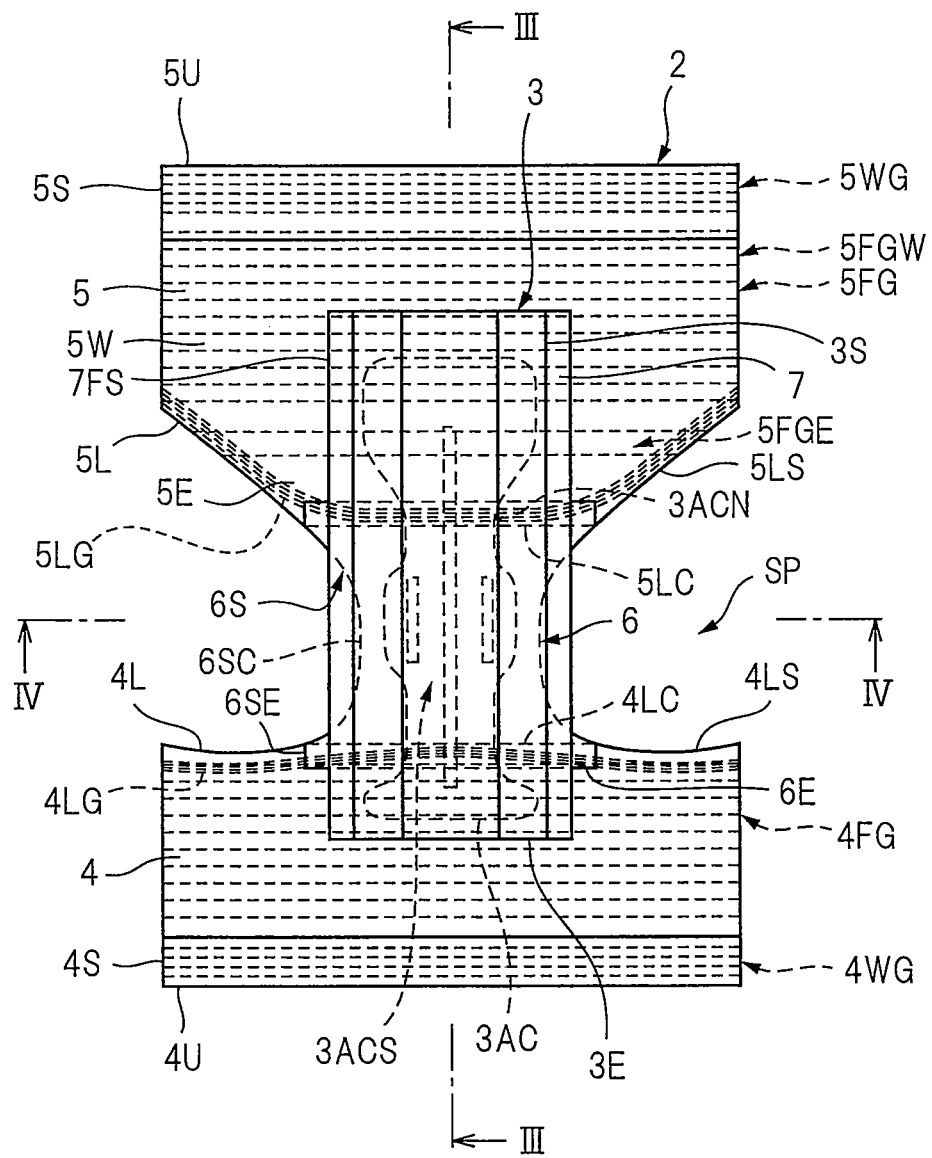
FIG. 2 is a plan view of a diaper that has been opened up by unfastening joining portions positioned at side areas.
Figure 2:
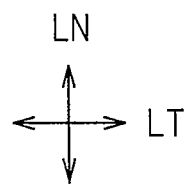

With reference to FIG. 2 showing the diaper 1 when opened up, the front piece 4 has a rectangular shape. The upper edge 4U of the front piece 4 extends linearly in the transverse direction LT. On the other hand, the lower edge 4L of the front piece 4 is provided with a central portion 4LC positioned substantially in the center in the transverse direction LT and side portions 4LS on both sides in the transverse direction LT of the central portion 4LC, the central portion 4LC extends substantially in transverse direction LT, and the side portions 4LS are slightly curved towards the upper edge 4U. In addition, both side edges 4S in the transverse direction of the front piece 4 extend substantially in a longitudinal direction LN. The longitudinal direction LN is perpendicular to the transverse direction LT.

In addition, the back piece 5 has a hexagonal shape protruding towards the front piece 4. Namely, the back piece 5 is provided with a rectangular waist portion 5W and a trapezoidal extending portion 5E that extends from the waist portion 5W towards the front piece 4. The upper edge of the back piece 5, namely the upper edge 5U of the waist portion 5W, extends substantially in the transverse direction LT. On the other hand, the lower edge of the back piece 5, namely the lower edge 5L of the extending portion 5E, is provided with a central portion 5LC positioned substantially in the center in the transverse direction LT and side portions 5LS on both sides in the transverse direction LT of the central portion 5LC, the central portion 5LC extends substantially in the transverse direction LT, and the side portions 5LS are slightly curved towards the upper edge 5U while extending at an angle with respect to the transverse direction LT. In addition, both side edges 5S in the transverse direction of the back piece 5 extend substantially in the longitudinal direction LN.

When opened up as shown in FIG. 2, the front piece 4 and the back piece 5 are arranged while separated by a spacing area SP in the longitudinal direction LN perpendicular to the transverse direction LT. The connecting sheet 6 extends in the longitudinal direction LN by straddling this spacing area SP substantially in the center in the transverse direction LT of the front piece 4 and the back piece 5, and is respectively anchored to the front piece 4 around the lower edge 4L and the back piece 5 around the lower edge 5L, namely the extending portion 5E.

The connecting sheet 6 has a shape in which narrowed portions are provided in both sides of a rectangular shape substantially in the center in the longitudinal direction LN. In this case, the length and/or width of the connecting sheet 6 in the transverse direction LT is shorter than the width of the front piece 4 and the back piece 5 in the transverse direction LT, and the length of the connecting sheet 6 in the longitudinal direction LN is also shorter than the length of the inner body 3 in the longitudinal direction LN. In addition, the side edges 6S of the connecting sheet 6 are provided with a central portion 6SC substantially in the center in the longitudinal direction LN and end portions 6SE positioned on both sides in the longitudinal direction of the central portion 6SC, the central portion 6SC is curved inward, and the end portions 6SE extend substantially in the longitudinal direction LN. In other words, the end portions 6SE do not coincide with the edges of the outer body 2 that define the leg holes 1L, namely the lower edge 4L of the front piece 4 and the lower edge 5L of the back piece 5, but rather are positioned farther to the inside in the transverse direction LT than the lower edges 4L and 5L. Note that the end portions 6SE correspond to both edges in the transverse direction LT of the portions of the connecting sheet 6 that overlap with the front piece 4 and the back piece 5. In addition, both end edges 6E in the longitudinal direction LN of the connecting sheet 6 extend substantially in the transverse direction LT.

On the other hand, the inner body 3 has a rectangular shape that extends in the longitudinal direction LN. Both side edges 3S in the transverse direction LT of the inner body 3 extend substantially in the longitudinal direction LN, while both end edges 3E in the longitudinal direction LN extend substantially in the transverse direction.

In addition, a pair of leakage preventing members 7 is provided on both sides in the transverse direction LT of the inner body 3 along both side edges 3S of the inner body 3. The free edges and/or outer edges 7SO in the transverse direction LT of the leakage preventing members 7 extend in the longitudinal direction LN.

As was previously described, the inner body 3 is overlapped and anchored on the connecting sheet 6. In this case, the inner body 3 extends in the longitudinal direction LN beyond the connecting sheet 6 and is also anchored to the front piece 4 and the back piece 5.

In addition, in this case, at least a portion of the central portion 6SC of both side edges 6S of the connecting sheet 6 are positioned farther to the inside in the transverse direction LT than the outer edges 7SO of the leakage preventing members 7, and are also positioned farther to the inside in the transverse direction LT than both side edges 3S of the inner body 3. In contrast, the end portions 6SE of both side edges 6S are positioned farther to the outside in the transverse direction LT than both side edges 3S of the inner body 3, and are also positioned farther to the outside in the transverse direction LT than the outer edges 7SO of the leakage preventing members 7.

Figure 3:
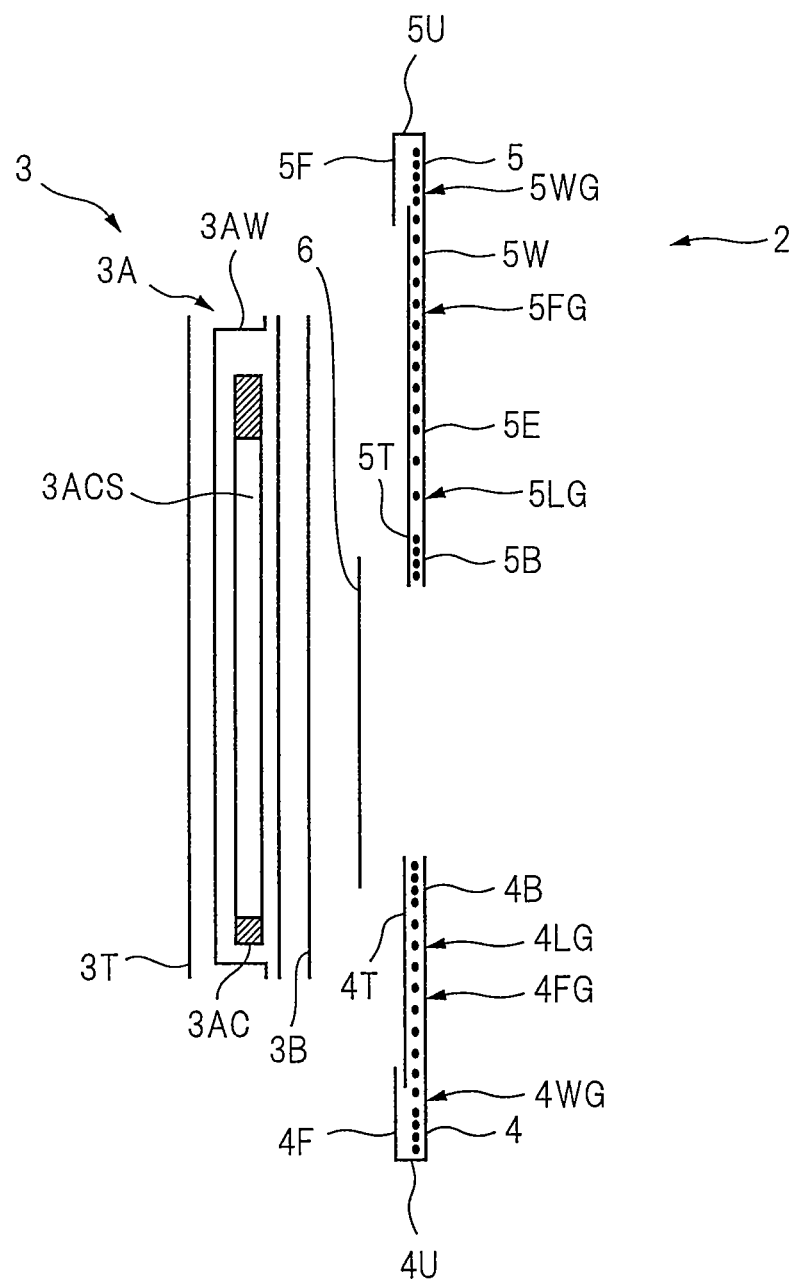
FIG. 3 is a longitudinal cross-sectional view taken along line of FIG. 2.

As shown in FIG. 3, the front piece 4 is provided with two sheets, namely, a top sheet 4T that faces the wearer when worn and a back sheet 4B that faces to the outside when worn, and the top sheet 4T and the back sheet 4B are mutually overlapped. Similarly, the back sheet 5 is also provided with two sheets, namely, a top sheet 5T that faces the wearer when worn and a back sheet 5B that faces to the outside when worn, and the top sheet 5T and the back sheet 5B are mutually overlapped.

On the other hand, the connecting sheet 6 is formed from a single sheet. The sheet in this case may be liquid permeable or liquid impermeable.

This being the case, the connecting sheet 6 is softer than the front piece 4 and the back piece 5. Note that the quantity, material or basis weight and the like of the sheet that forms the connecting sheet 6 can be selected so as to be softer than the front piece 4 and the back piece 5. The degree of softness of the sheet material can be measured by, for example, a cantilever method.

In addition, in the example shown in FIG. 2, the connecting sheet 6 is attached to the inside and/or wearer side of the front piece 4 and the back piece 5, namely to the top sheets 4T and 5T. However, the connecting sheet 6 may also be attached to the outside of the front piece 4 and the back piece 5, namely to the back sheets 4B and 5B. Alternatively, the areas around both ends in the longitudinal direction LN of the connecting sheet 6 may be made to be sandwiched between the top sheets 4T and 5T and between the back sheets 4B and 5B. Whereupon, both areas around the ends of the connecting sheet in the longitudinal direction LN are not exposed on the sides of the top sheets 4T and 5T or the back sheets 4B and 5B, thereby resulting in better touch to the skin. In addition, the connecting sheet 6 is more resistant to separation from the front piece 4 and the back piece 5.

Here, the top sheets 4T and 5T and back sheets 4B and 5B of the front piece 4 and the back piece 5 as well as the connecting sheet 6 are each a non-woven fabric formed from synthetic fibers such as polyolefin-based fibers in the manner of polypropylene (PP) or polyethylene (PE) or polyethylene terephthalate (PET)-based fibers, are formed from a non-woven fabric manufactured by spunbonding or air-through bonding, and each has a basis weight of, for example, 13 g/m² to 30 g/m². In the first embodiment according to the present invention, the top sheets 4T and 5T are respectively formed from an SMS non-woven fabric having a basis weight of 15 g/m² formed from PSS, the back sheets 4B and 5B are respectively formed from a spun-bonded non-woven fabric having a basis weight of 17 g/m² formed from PP, and the connecting sheet 6 is formed from an SMS non-woven fabric having a basis weight of 15 g/m² formed from PP.

In addition, an elastic member 4WG is provided in the front piece 4 around the upper edge 4U, an elastic member 4LG is provided in the front piece 4 around the lower edge 4L, and an elastic member 4FG is provided in the front piece 4 between the elastic member 4WG and the elastic member 4LG. As shown in FIG. 3, a folded portion 4F is provided around the upper edge 4U in which the back sheet 4B is folded to the side of the top sheet 4T, and the elastic member 4WG is anchored between the back sheets 4B at the folding portion 4F. On the other hand, the elastic members 4FG and 4LG are anchored between the top sheet 4T and the back sheet 4B.

Similarly, an elastic member 5WG is provided in the back piece 5 around the upper edge 5U, an elastic member 5LG is provided in the back piece 5 around the lower edge 5L, and an elastic member 5FG is provided in the back piece 5 between the elastic member 5WG and the elastic member 5LG. A folded portion 5F is provided around the upper edge 5U in which the back sheet 5B is folded to the side of the top sheet 5T, and the elastic member 5WG is anchored between the back sheets 5B at the folding portion 5F. On the other hand, the elastic members 5FG and 5LG are anchored between the top sheet 5T and the back sheet 5B. These elastic members 4WG, 4FG, 4LG, 5WG, 5FG and 5LG are in the form of threads, for example, and are attached to the front piece 4 and the back piece 5 in a stretched state.

In this case, the elastic member 5FG includes an elastic member 5FGW provided in the waist portion 5W of the back piece 5 and an elastic member 5FGE provided in the extending portion 5E. As can be understood from FIG. 2, the elastic member 5FGE is provided overlapping the inner body 3 and the leakage preventing member 7. This elastic member 5FGE provides elastic action between the side areas 1F and crotch area 10 of the diaper 1 when worn.

In addition, the elastic members 4LG and 5LG extend continuously without being interrupted in the front piece 4 and the back piece 5, and are provided overlapping with the outer body 3, the connecting sheet 6 and the leakage preventing members 7. These elastic members 4LG and 5LG also provide elastic action between the side areas 1F and the crotch area 10 of the diaper when worn.

Note that the upper edges of the top sheets 4T and 5T are arranged roughly along the lower edges of the elastic members 4WG and 5WG, while the lower edges of the top sheets 4T and 5T are arranged roughly along the lower edges of the back sheets 4B and 5B.

The elastic members 4WG, 4FG, 4LG, 5WG, 5FG and 5LG are formed from elastic fibers in the manner of natural rubber, synthetic rubber or spandex fibers, and have a draw ratio of, for example, 1.3 to 3.5. In the case the elastic members 4WG, 4FG, 4LG, 5WG, 5FG and 5LG are formed from spandex, the thickness of the elastic members 4WG, 4FG, 4LG, 5WG, 5FG and 5LG is, for example, 300 dtex to 1200 dtex. In the first embodiment according to the present invention, the elastic members 4WG and 5WG are respectively formed from spandex having a thickness of 940 dtex and draw ratio of 3.0, the elastic members 4FG and 5FG are formed from spandex having a thickness of 780 dtex and draw ratio of 2.5, the elastic members 4LG are formed from spandex having an average draw ratio of 2.5, and the elastic members 5LG are formed from spandex having an average draw ratio of 2.2. In addition, the elastic member 4WG and the elastic member 5WG respectively contain 5 spandex fibers, the elastic member 4FG contains 10 spandex fibers, the elastic member 5FGW of the waist portion 5W contains 11 spandex fibers, and the elastic member 5FGE of the extending portion 5E contains 2 spandex fibers. Note that the elastic members 4WG, 4FG, 4LG, 5WG, 5FG and 5LG may also be formed from elastic sheets.

Figure 4:
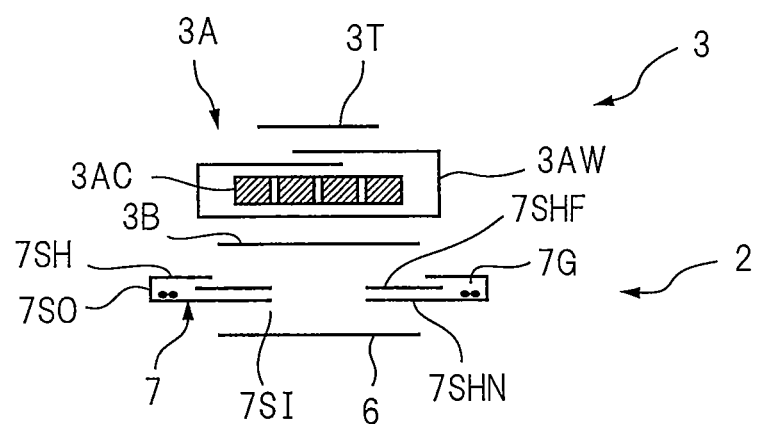
FIG. 4 is a lateral cross-sectional view taken along line IV-IV of FIG. 2.

As is shown in FIGS. 3 and 4, the inner body 3 is provided with a liquid permeable top sheet 3T, a liquid impermeable back sheet 3B and an absorptive body 3A arranged between the top sheet 3T and the back sheet 3B. In addition, the absorptive body 3A is provided with an absorptive body core 3AC and a wrapping sheet 3AW that envelops the absorptive body core 3AC.

Widened portions 3ACW are formed on both ends in the lengthwise direction and/or longitudinal direction LN of the absorptive body core 3AC and at an intermediate portion between both ends, and these widened portions 3ACW are mutually connected by narrowed portions 3ACN.

In addition, a plurality of slits 3ACS are provided in the absorptive body core 3AC that extend in the lengthwise direction and/or longitudinal direction LN. These slits 3ACS include a central slit positioned substantially in the center in the transverse direction LT, and side slits positioned on both sides of the central slit. In the first embodiment according to the present invention, the length of the central slit is 320 mm and the width is 12 mm, while the length of the side slits is 80 mm and the width is 10 mm. This being the case, the absorptive body core 3AC easily bends along the slits 3ACS, thereby facilitating adherence of the absorptive body 3A to the wearer.

The top sheet 3T is formed from a hydrophilic non-woven fabric formed from polyolefin-based fibers or PET fibers and the like that is manufactured by a manufacturing method such as spunbonding or air-through bonding. The back sheet 3B is formed from a water-resistant and moisture-permeable film formed from PE and the like. The absorptive body core 3AC is formed from pulp, superabsorbent polymer (SAP) or mixture thereof. The wrapping sheet 3AW is formed from a hydrophilic non-woven fabric formed from polyolefin-based fibers or PET fibers and the like that is manufactured by a manufacturing method such as spunbonding or air-through bonding. In the first embodiment according to the present invention, the top sheet 3T is formed from a non-woven fabric manufactured by air-through bonding and having a basis weight of 25 $g/m^2$, the back sheet 3B is formed from a moisture-permeable PET film having a basis weight of 22 $g/m^2$, the absorptive body core 3AC is formed from a single mixed layer of pulp having a basis weight of 250 $g/m^2$ and SAP having a basis weight of 200 $g/m^2$, and the wrapping sheet 3AW is formed from an SMS non-woven fabric having a basis weight of 13 $g/m^2$.

As is shown in FIG. 4, each of the leakage preventing members 7 has anchored edges and/or inner edges 781 anchored to the outer body 2 or the inner body 3, and free edges and/or outer edges 780 not anchored to the outer body 3 or the inner body 2. In addition, each of the leakage preventing members 7 includes a liquid impermeable sheet 7SH and elastic members 7G, and the liquid impermeable sheet 78H includes a leakage preventing non-woven fabric 7SHN and a leakage preventing film 78HF. In the outer edges 780 of each of the leakage preventing members 7, the leakage preventing non-woven fabric 78HN is folded and overlaps the outer edges of the leakage preventing film 7SHF, and the elastic members 7G are anchored between the folded leakage preventing non-woven fabric 7SHN. Note that the outer edges of the leakage preventing film 7SHF do not reach to the outer edges 7S0 of the leakage preventing members 7. On the other hand, in the inner edges 7SI of each of the leakage preventing members 7, the edges of the leakage preventing non-woven fabric 7SHN and the leakage preventing film 7SHF are substantially mutually arranged in rows.

When worn, each of the leakage preventing members 7 rises up towards the wearer to act as leakage preventing barriers.

The leakage preventing non-woven fabric 7SHN is formed from polyolefin-based fibers or PET fibers and the like, and is manufactured by a method such as spun bonding. The leakage preventing film 7SHF is formed from polyethylene (PE) or PET and the like. In the first embodiment according to the present invention, the leakage preventing non-woven fabric 7SHN is formed from hydrophobic SMS non-woven fabric having a basis weight of 15 $g/m^2$, and the leakage preventing film 7SHF is formed from a moisture-permeable PE film having a basis weight of 18 $g/m^2$. The elastic members 7G are formed from elastic fibers in the manner of natural rubber, synthetic rubber or spandex fibers. In the first embodiment according to the present invention, the elastic members 7G are formed from two spandex fibers having a thickness of 620 dtex and draw ratio of 2.2.

Connection and/or anchoring of these members are carried out by, for example, heat sealing, sonic sealing or an adhesive and the like. A hot melt adhesive (HMA) containing, for example, styrene-isoprene-styrene (SIS), styrene-butadiene-styrene (SBS) or styrene-ethylene-butylene-styrene (SEBS) adhesive can be used for the adhesive.

More specifically, the top sheets 4T and 5T and back sheets 4B and 5B of the front piece 4 and the back piece 5 are mutually connected to the elastic members 4WG, 4FG, 5WG and 5FG with a preliminarily applied HMA. In addition, at those locations where the elastic members 4WG, 4FG, 5WG and 5FG are sparse, namely where the interval between elastic members is, for example, 10 mm or more, HMA is applied to the top sheets 4T and 5T and the back sheets 4B and 5B by a coating method in the manner of spiral coating or controlled seam coating. Moreover, HMA is also applied to the top sheets 4T and 5T and the back sheets 4B and 5B around the lower edges 4L and 5L in order to prevent separation.

On the other hand, the elastic members 4LG and 5LG are anchored to the top sheets 4T and 5T by HMA preliminarily applied to the top sheets 4T and 5T by a coating method such as spiral coating. In this case, the HMA is applied so as to follow the loci of the elastic members 4LG and 5LG.

In addition, the connecting sheet 6 is connected to the front piece 4 and the back piece 5 by a method such as sonic sealing or adhesive. In the first embodiment according to the present invention, HMA is preliminarily applied to the back of the connecting sheet 6 by a coating method such as slot coating.

On the other hand, in the inner body 3, the top surface and bottom surface of the absorptive body core 3AC are connected to the core wrapping sheet 3AW by an adhesive such as HMA. In this case, the adhesive is applied by a coating method such as spiral coating, slot coating, controlled seam coating, bead coating or curtain coating so as to have a basis weight of 1.5 $g/m^2$ to 10 $g/m^2$. In the first embodiment according to the present invention, HMA is applied by a spiral coating method so as to have a basis weight of 5 $g/m^2$.

In addition, HMA is applied to the back sheet 3B of the inner body 3 or side of the leakage preventing members 7 facing the outer body 2 by a controlled seam coating method, and as a result thereof, the inner body 3 and the leakage preventing members 7 are anchored to the front piece 4, the back piece 5 and the connecting sheet 6.

In the leakage preventing members 7, HMA is applied to the elastic members 7G by a slit nozzle method, and the elastic members 7G are anchored to the leakage preventing non-woven fabric 7SHN by this HMA. In addition, the leakage preventing non-woven fabric 7SHN and the leakage preventing film 7SHF are mutually joined by applying HMA to the leakage preventing non-woven fabric 7SHN by spiral coating.

Note that, in the side areas 1F of the diaper 1, the front piece 4 around both side edges 4S and the back piece 5 around both side edges 5S are mutually joined by a method such as heat sealing or ultrasonic sealing. Note that the front piece 4 and the back piece 5 may be refastenably joined, and in this case, mechanical fasteners containing hooks and loops can be used.

The edges 1LE that define the legs holes 1L are formed by the side portions 4LS of the lower edge 4L of the front piece 4, the side portions 5LS of the lower edge 5L of the back piece 5, and both edges 6S of the connecting sheet 6. In this case, the edges 1LE are formed by a single cutting action and are smoothly curved and continuing.

In the first embodiment according to the present invention, at least a portion of both side edges 6S of the connecting sheet 6 are positioned farther to the inside in the transverse direction LT than both side edges 3S of the inner body 3 in the spacing area SP between the front piece 4 and the back piece 5 as was previously described. Thus, the range of movement of the legs of a wearer can be increased while maintaining a large absorptive surface for the inner body 3. Namely, difficulty encountered by a wearer when moving the legs can be inhibited while maintaining favorable absorptive performance of the inner body 3.

At the same time, the end portions 6SE of the connecting sheet 6 are positioned farther to the outside in the transverse direction LT than both side edges 3S of the inner body 3 (FIG. 2). As a result, the front piece 4 and the back piece 5 can be reliably connected to the connecting sheet 6 while facilitating movement of the legs of a wearer.

Moreover, since the extending portion 5E having the elastic member 5FGE is provided in the back piece 5, the shape of the diaper 1 can be made to be that of an undergarment, and the entire gluteal region of the wearer is covered by the back piece 5. Thus, leakage can be suppressed and apprehension of the wearer concerning leakage can be reduced.

Moreover, since the inner body 3 is pulled up towards the side areas 1F (FIG. 1) by the elastic members 5FGE, 4LG and 5LG, twisting of the inner body 3 to the inside is suppressed, thereby maintaining absorptive properties of the inner body 3.

What is more, since the edges 1LE that define the leg holes 1L are continuing by curving smoothly, they have a curved shape that follows the legs of a wearer, thereby enhancing adherence to the wearer.

Moreover, the length of the connecting sheet 6 can be shorter than the length of the inner body 3. Thus, the amount of the connecting sheet 6 can be decreased, thereby making it possible to reduce costs.

Moreover, the connecting sheet 6 is softer than the front piece 4 and the back piece 5 as was previously described. As a result, in comparison with the case of having two sheets in the crotch area 1C as a result of the entire outer body 2 being provided with a top sheet and a back sheet, the connecting sheet and/or inner body 2 makes soft contact with the legs and/or groin region of a wearer and the legs of the wearer become easier to move. In addition, even if the outer body 2 rolls up and becomes wrinkled, the wearer is less likely to feel a sense of tightness. Moreover, since the connecting sheet 6 is formed from a single sheet, costs can be reduced in comparison with the case of the entire outer body 2 being formed from a top sheet and back sheet.

In addition, since the connecting sheet 6 can be formed from a material differing from that of the front piece 4 and the back piece 5, cost performance of the diaper 1 can be enhanced. Namely, if the connecting sheet 6 is formed from a moisture permeable or moisture absorptive material, breathability in the crotch area 1C can be improved. A non-woven fabric containing cellulose-based fibers such as rayon or pulp and polyester fibers can be used as a moisture absorptive material. More specifically, a non-woven fabric containing rayon, polyolefin-based fibers and polyester fibers (such as a non-woven fabric manufactured by spun lacing and having a basis weight of 26 g/m$^2$) or a non-woven fabric containing pulp and polyester (such as a non-woven fabric manufactured by spun lacing and having a basis weight of 40 g/m$^2$) is used.

In addition, twisting of the inner body 3 to the inside can be suppressed by providing the connecting sheet 6. Consequently, the leakage preventing members 7 reliably rise up towards the wearer. Namely, the connecting sheet 6 provides a starting point for the leakage preventing members 7 to rise up towards the wearer.

Figure 5:
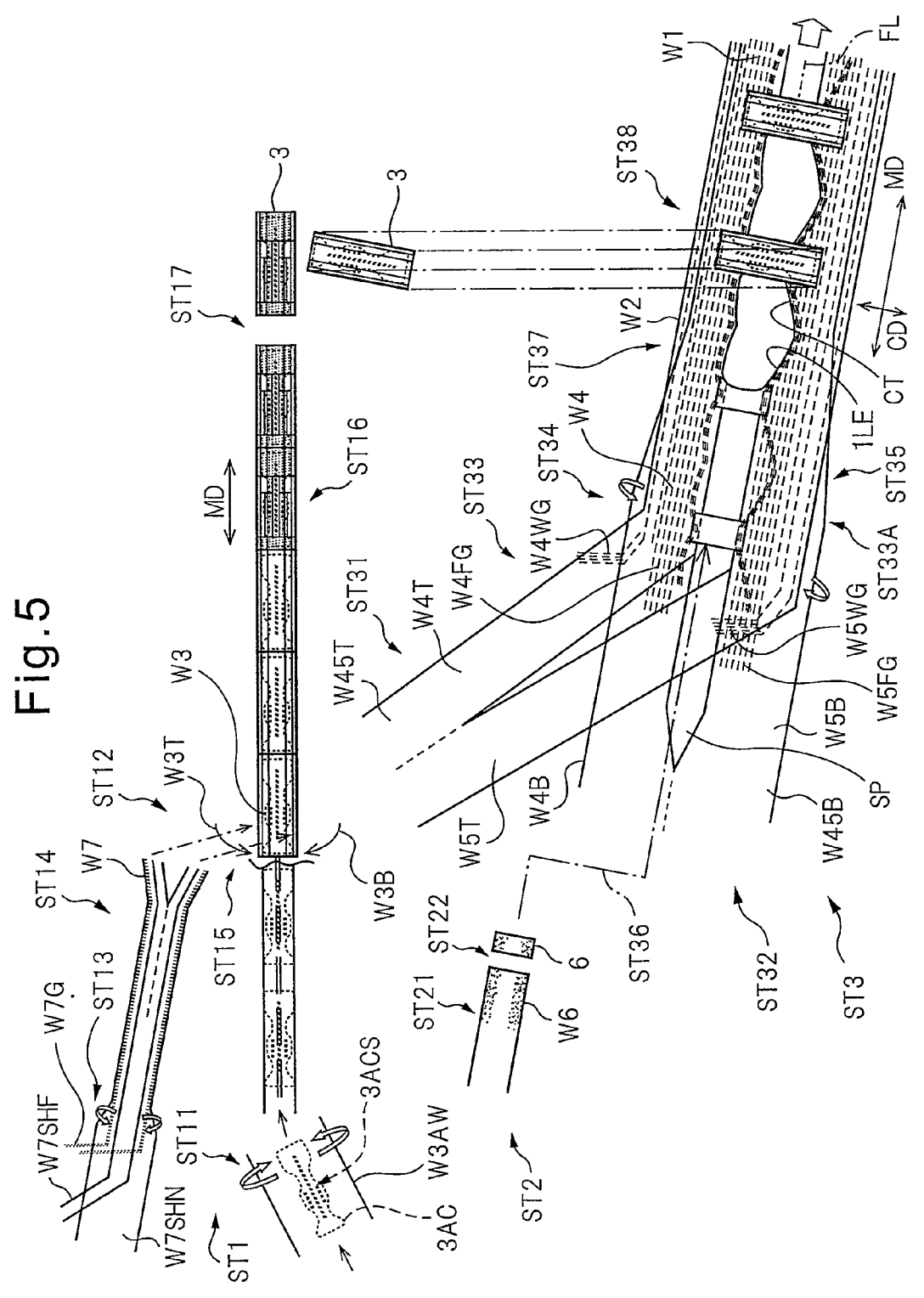

Next, an explanation is provided of the manufacturing method of the diaper 1 of the first embodiment according to the present invention with reference to FIG. 5.

With reference to FIG. 5, the manufacturing method of the first embodiment according to the present invention comprises a step ST1 for manufacturing the inner body 3 provided with the leakage preventing members 7, a step ST2 for manufacturing the connecting sheet 6, and a step ST3 for manufacturing a continuous body of the diaper 1 in the form of a web W1.

In the step ST1, the absorptive body core 3AC in which the slits SACS have been preliminarily formed is first wrapped with a continuous body of the wrapping sheet 3AW in the form of a wrapping sheet web W3AW (ST11). Note that, in this case, the absorptive body core 3AC is transported so that the slits 3ACS are parallel to a machine direction MD.

Next, continuous bodies of the top sheet 3T and back sheet 3B in the form of top sheet web W3T and back sheet web W3B are respectively affixed to the upper surface and lower surface of the wrapping sheet web W3AW wrapped around the absorptive body core 3AC to form a continuous body of the inner body 3 in the form of an inner body web W3 (ST12).

On the other hand, a continuous body equivalent to two leakage preventing films 7SHF in the form of a leakage preventing film web W7SHF and a continuous body of the elastic members 7G in the form of continuous elastic bodies W7G are attached to a continuous body equivalent to two leakage preventing non-woven fabrics 7SHN in the form of a leakage preventing non-woven fabric web W7SHN (ST13). Next, the leakage preventing non-woven fabric web W7SHN is divided along the machine direction MD to form a continuous body of the leakage preventing members 7 in the form of leakage preventing member webs W7 (ST14).

Next, each leakage preventing member web W7 is affixed to the back of the inner body web W3, namely the back sheet web W3B (ST15).

Next, HMA is applied in a predetermined pattern to the back of the inner body web W3 and the leakage preventing member webs W7, namely the side opposing an outer body web W2 (ST16).

Next, the inner body web W3 and the leakage preventing member webs W7 are cut to the length of a single finished product to form the inner body 3 provided with the leakage preventing members 7 (ST17).

In step ST2, HMA is applied to the bottom of a continuous body of the connecting sheet 6 in the form of a connecting sheet web W6 (ST21).

Next, the connecting sheet web W6 is cut to the length of a single finished product to form the connecting sheet 6 (ST 22).

In step ST3, a top sheet web W45T is divided along the machine direction MD to form a continuous body of the top sheet 4T of the front piece 4 in the form a top sheet web W4T and a continuous body of the top sheet 5T of the back piece 5 in the form of a top sheet web W5T (ST31). Similarly, a back sheet web W45B is divided along the machine direction MD to form a continuous body of the back sheet 4B of the front piece 4 in the form of a back sheet web W4B and a continuous body of the back sheet 5 of the back piece 5 in the form of a back sheet web W5B (ST32). The top sheet web W4T and the back sheet web W5B are transported along the machine direction MD separated by the spacing area SP in a cross-machine direction CD substantially perpendicular to the machine direction MD.

In addition, continuous bodies of the elastic members 4WG and 5WG in the form of continuous elastic bodies W4WG and W5WG as well as continuous bodies of the elastic members 4FG and 5FG in the form of continuous elastic bodies W4FG and W5FG are respectively attached to the back sheet webs W4B and W5B while being stretched in the machine direction MD (ST33).

In addition, continuous bodies of the elastic members 4LG and 5LG in the form of continuous elastic bodies W4LG and W5LG are respectively attached to the top sheet webs 4WT and W5T while being stretched at substantially the same location at which the continuous elastic bodies W4WG, W5WG, 4FG and W5FG are supplied (ST33A). Note that, in FIG. 5, the continuous elastic bodies W4LG and W5LG are depicted as being attached to the back sheet webs W4B and W5B for the sake of legibility. In addition, the continuous elastic bodies W4LG and W5LG may also be attached to the back sheet web W4B and W5B.

Next, the top sheet webs W4T and W5T are respectively overlapped and pressed onto the back sheet webs W4B and W5B to form continuous bodies of the front piece 4 and the back piece 5 in the form of a front piece web W4 and a back piece web W5 (ST34). As a result, the continuous bodies W4WG, W5WG, W4FG, W5FG, W4LG and W5LG are held on the back sheet webs W4B and W5B and the top sheet webs W4T and W5T.

In addition, the outer edges of the back sheet webs W4B and W5B are folded to form folded portions 5F (ST35).

In addition, the connecting sheet 6 is attached to the front piece web W4 and the back piece web W5 at intervals in the machine direction MD so as to straddle the spacing area SP, and as a result thereof, a continuous body of the outer body 2 in the form of the outer body web W2 is formed (ST36).

Note that, in the case of making the areas around both ends of the connecting sheet 6 in the longitudinal direction LN to be sandwiched between the top sheets 4T and 5T and the back sheets 4B and 5B, the connecting sheet 6 is first attached to the top sheet webs W4T and W5T, after which the back sheet webs W4B and W5B are overlapped with the connecting sheet 6 and the top sheet webs W4T and W5T. Alternatively, the connecting sheet 6 is first attached to the back sheet webs W4B and W5B, after which the top sheet webs W4T and W5T are overlapped with the connecting sheet 6 and the back sheet webs W4B and W5B.

Next, a cutting action is carried out on the outer body web W2 at an interval in the machine direction MD to form the edges 1LE that define the leg holes 1L (ST37). In this case, the front piece web W4 and the back piece web W5 are cut along the elastic members 4LG and 5LG. In addition, the connecting sheet 6 is cut so that both side edges 6S of the connecting sheet 6 are curved inward, or so that at least a portion of both side edges 6S of the connecting sheet 6 in the spacing area SP are positioned farther to the inside in the transverse direction LT than both side edges 3S of the inner body 3. Note that cutting action is carried out once along an annular cutting line CT, for example. The trimmed material is recovered in this case.

Next, the inner body 3 provided with the leakage preventing members 7 is attached to the front piece web W4, the back piece web W5 and the connecting sheet 6 to form the diaper web W1 (ST38). Note that guides are preferably provided immediately before the cutting action and action for attaching the inner body 3 so that the position of the outer body web W2 in the cross-machine direction CD is at the proper position.

Next, the diaper web W1 is folded along a folding line FL lying in the machine direction MD (not shown). In this case, the folding line FL may be in the center of the diaper web W1 in the cross-machine direction CD or may be shifted from the center.

Next, the front piece web W4 and the back piece web W5 are partially joined at intervals in the machine direction MD to form joined portions as a result thereof. Next, the diaper web W1 is cut at these joined portions in the cross-machine direction CD to form the diaper 1 (not shown).

Figure 6:
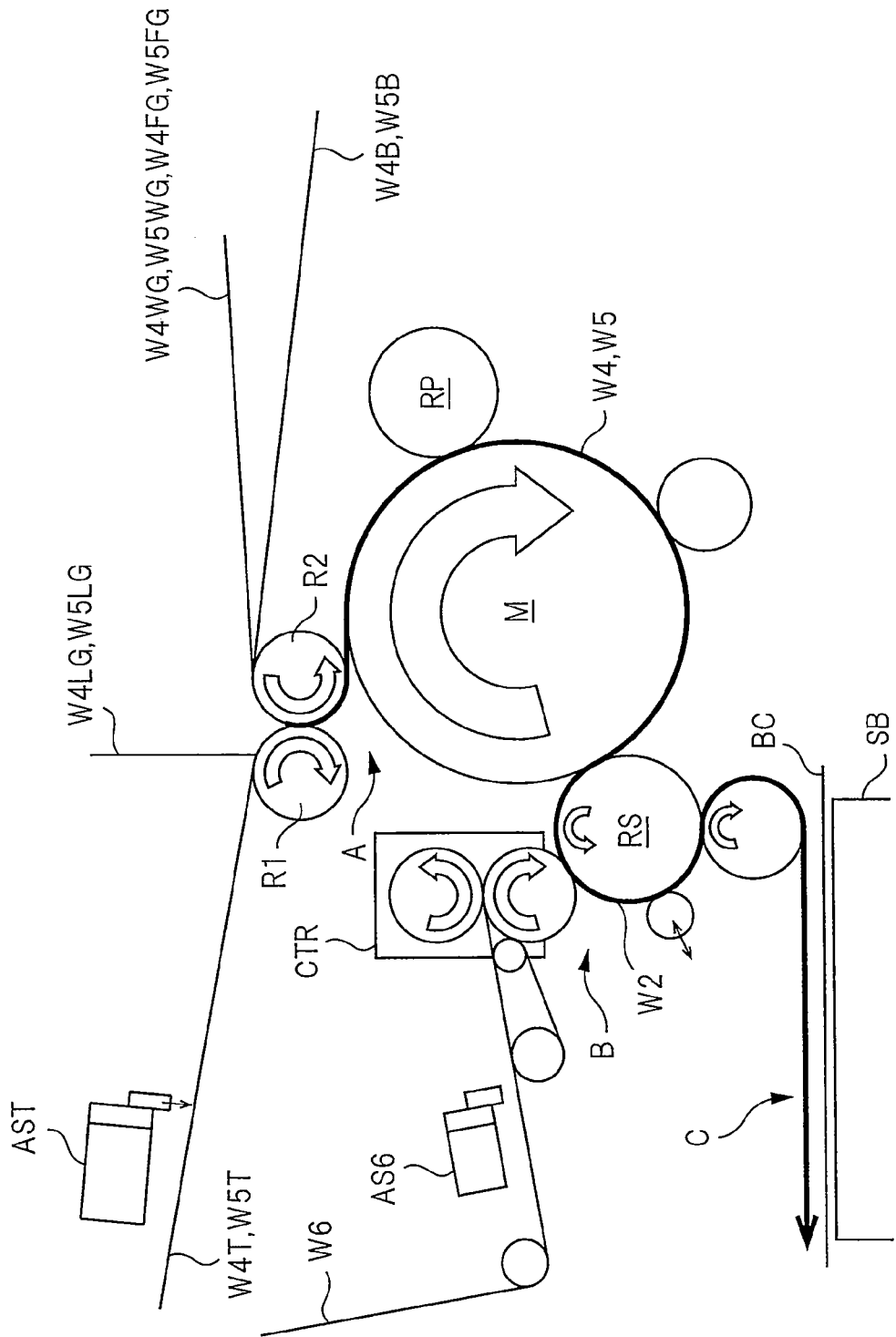
FIG. 6 is partial schematic diagram for explaining a method of manufacturing diapers.

In providing an explanation of steps ST33A, ST34, ST36 and the like with reference to FIG. 6, the top sheet webs W4T and W5T are respectively transported towards a roller R1, while the back sheet webs W4B and W5B are respectively transported towards a roller R2.

Prior to reaching the roller R1, the stretched continuous elastic bodies W4LG and W5LG are supplied and attached to the top sheet webs W4T and W5T while oscillating in the cross-machine direction. In addition, prior to this, HMA is supplied from an HMA applicator AST to the top sheet webs W4T and W5T so as to match the loci of the continuous elastic bodies W4LG and W5LG. On the other hand, prior to reaching the roller R2, stretched continuous elastic bodies W4WG, W5WG, W4FG and W5FG are supplied to the back sheet webs W4B and W5B.

Since the rollers R1 and R2 are mutually adjacent, the top sheet webs W4T and W5T and the back sheet webs W4B and W5B are overlapping on the rollers R1 and R2, respectively. At this time, the continuous elastic bodies W4WG, W5WG, W4FG, W5FG, W4LG and W5LG are sandwiched between the top sheet webs W4T and W5T and the back sheet webs W4B and W5B. Note that, as was previously described, HMA is preliminarily applied to the continuous elastic bodies W4WG, W5WG, W4FG and W5FG, and the continuous elastic bodies W4WG, W5WG, W4FG and W5FG are attached to the top sheet webs W4T and W5T and the back sheet webs W4B and W5B by this HMA.

The mutually overlapped top sheet webs W4T and W5T and back sheet webs W4B and W5B are then transported by a main drum M and pressed together by a press roller RP. As a result, the continuous elastic bodies W4WG, W5WG, W4FG, W5FG, W4LG and W5LG are attached to the top sheet webs W4T and W5T and the back sheet webs W4B and W5B to form the front piece web W4 and the back piece web W5. The front piece web W4 and the back piece web W5 then reach a suction transfer roller RS and are transported while being suctioned and held thereby.

On the other hand, following application of HMA by the HMA applicator AS6, the connecting sheet web W6 is transported to a cutter CTR and cut to form the connecting sheet 6. This connecting sheet 6 is discontinuously attached to the front piece web W4 and the back piece web W5 on the suction transfer roller RS. The outer body web W2 is formed in this manner.

Next, the outer body web W2 is transported by a belt conveyor BC traveling over a suction box SB. This being the case, the outer body web W2 can be suppressed from shifting out of position and forming wrinkles. Note that the suction box SB is preferably formed so that suction action is applied to the front piece web W4 and the back piece web WS without being applied to the spacing area SP.

Figure 7A:
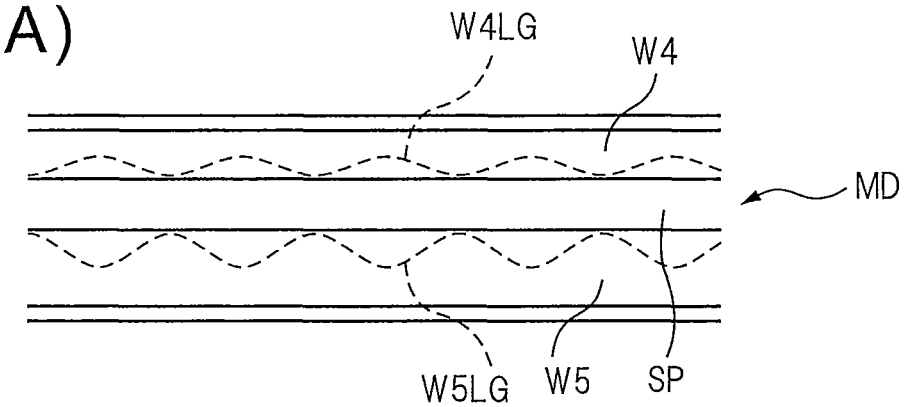
FIGS. 7(A), 7(B) and 7(C) are drawings of a top sheet web as viewed from arrows A, B and C of FIG. 6.
Figure 7B:
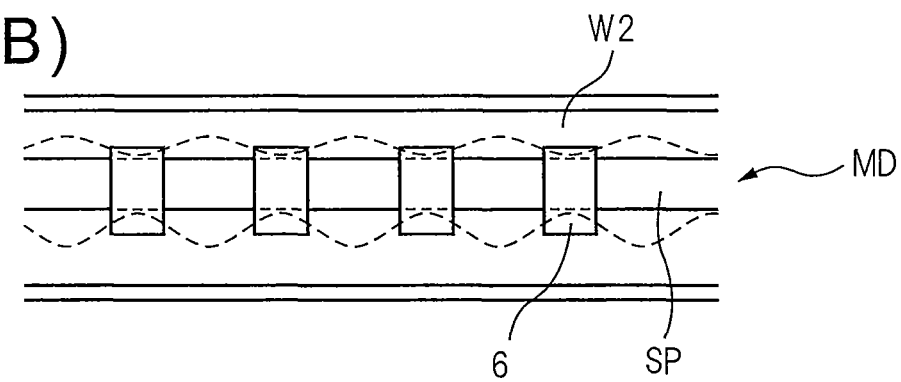
Figure 7C:
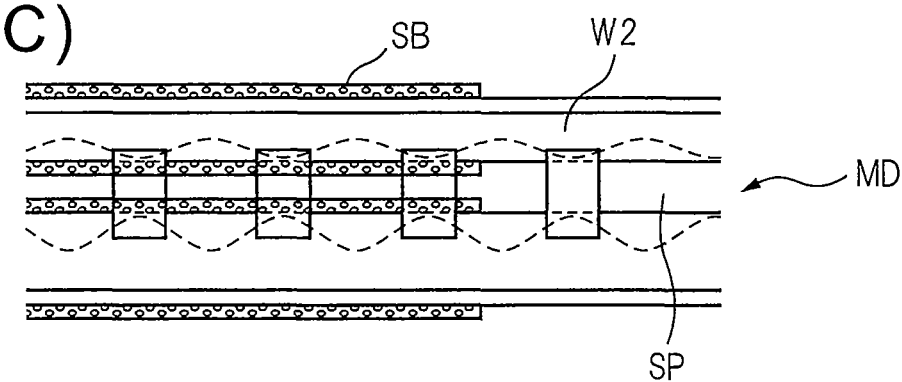

The top sheet webs 4WT and 5WT as viewed from arrows A, B and C in FIG. 6 are respectively shown in FIGS. 7(A), 7(B) and 7(C). Note that the continuous elastic bodies W4WG, W5WG, W4FG and W5FG are omitted from FIGS. 7(A), 7(B) and 7(C).

In this manner, in the first embodiment according to the present invention, cutting action for forming the edges ILE that define the leg holes 1L is carried out after the connecting sheet 6 is connected to the front piece web W4 and the back piece web W5. As a result, cutting action can be carried out with the outer body web W2, namely the front piece web W4 and the back piece web W5 mutually connected to the connecting sheet 6, free of wrinkles as a result of respectively pulling to the outside in the cross-machine direction CD. Thus, the leg holes 1L can be formed in the proper shape. In addition, the outer body 3 can be attached to the inner body web 2 without wrinkling. Thus, the inner body 3 can be reliably attached to the inner body web W2.

Namely, there is the risk of wrinkling of the front piece web W4 and the back piece web W5 in the state in which they are not mutually connected by the connecting sheet 6, and if cutting action is carried out while in this state, there is the risk of the edges 1LE that define the leg holes 1L deviating from the proper shape. In addition, it is also difficult to reliably attach the inner body 3 to the outer body web W2 while in this state. On the other hand, when cutting action is carried out, the front piece web W4 and the back piece web W5 around the edges 1LE that define the leg holes 1L become discontinuous in the machine direction MD. Since these discontinuous portions are not held in the machine direction MD, there is the risk of these portions being rolled up and flapping about, thereby causing wrinkling or flapping of the front piece web W4 and the back piece web W5. Moreover, when such discontinuous portions are formed, the continuous elastic bodies W4LG and W5LG, for example, of the front piece web W4 and the back piece web W5 contract in the cross-machine direction CD, again resulting in the risk of wrinkling or flapping of the front piece web W4 and the back piece web W5. When the connecting sheet 6 or the inner body 3 is attempted to be attached to the front piece web W4 and the back piece web W5 in which wrinkling or flapping has occurred, the connecting sheet 6 or the inner body 3 is not reliably connected to the front piece web W4 and the back piece web W5, thereby resulting in the risk of a decrease in productivity of the diaper 1.

In contrast, in the first embodiment of the present invention, after the front piece web W4 and the back piece web W5 are mutually connected by the connecting sheet 6, cutting action is carried out for forming the edges 1LE followed by attachment of the inner body 3. Thus, problems like those described above do not occur. Note that these problems are unique to methods of manufacturing the diaper 1 in which the front piece 4 and the back piece 5 are formed from separate sheets, and do not occur in methods of manufacturing diapers in which the front piece and the back piece are formed from a single sheet.

In addition, cutting action for forming the edges 1LE is not carried out on the inner body 3, thereby eliminating the risk of the inner body 3 being damaged by this cutting action. Thus, productivity of the diaper 1 can be maintained at a high level.

In addition, in the first embodiment according to the present invention, the connecting sheet 6 is not attached to the front piece web W4 and the back sheet web W5 in the form of a web, but rather is attached after having cut to an amount equivalent to a single finished product. As a result, costs incurred for the connecting sheet 6 can be reduced considerably. This is because, if the connecting sheet 6 is attached in the form of a web, the majority of the connecting sheet 6 ends up being removed by the cutting action.

Moreover, since the connecting sheet is attached discontinuously, the end portions 6SE can be positioned farther to the inside in the transverse direction LT than the side portions 4LS of the front piece 4 and the side portions 5LS of the back piece 5 that define the leg holes 1L. As a result, the connecting sheet 6 is not present around the side portions 4LS and 5LS, thereby improving comfort when worn.

Figure 21:
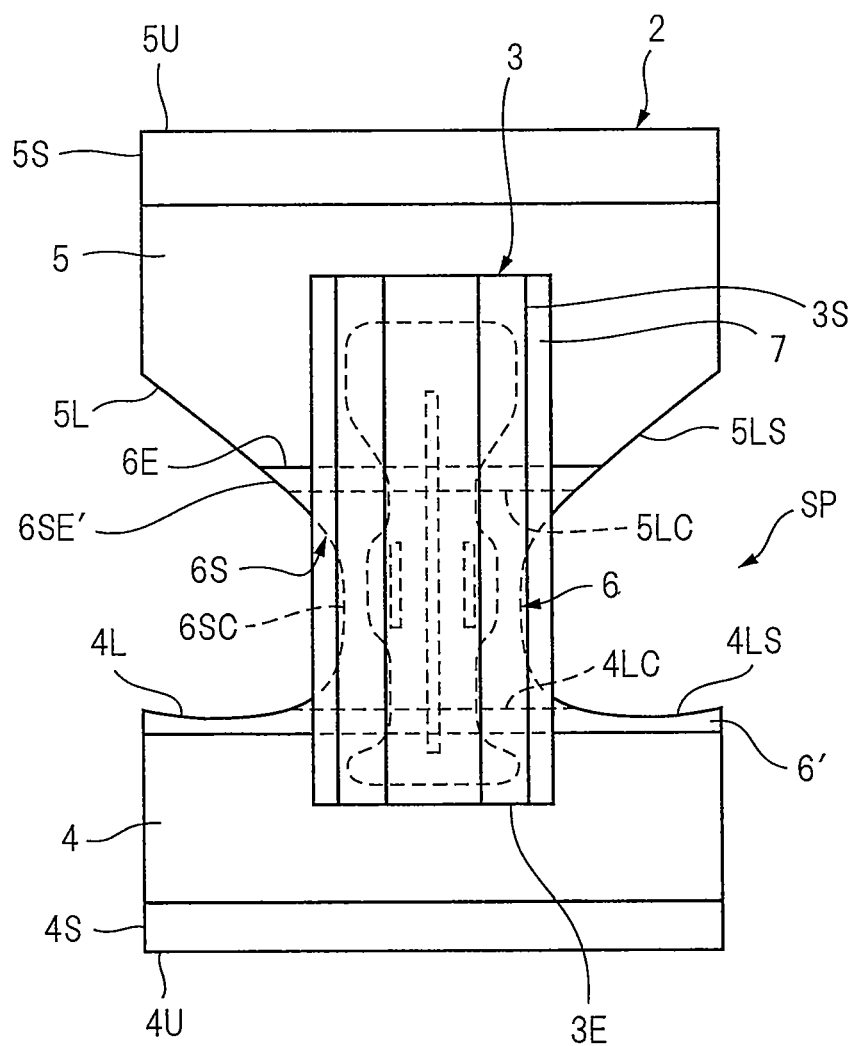
FIG. 21 is an open plan view for explaining an undesirable example of an end portion.
Figure 21:
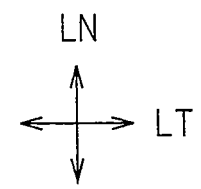

Namely, FIG. 21 shows the case of the connecting sheet web W6 being attached to the front piece web W4 and the back piece web W5, and in this case, end portions 6SE' on the side of the back piece 5 coincide with the side portions 5LS, and the connecting sheet 6 is therefore present around the side portions 5LS. In addition, portions 6' of the connecting sheet 6 that overlap the front piece 4 extend to the side edges 4S of the front piece 4 along the side portions 4LS, and the connecting sheet 6 is therefore present around the side portions 4LS. As a result, the areas around the side portions 4LS and 5LS become comparatively hard, thereby resulting in the risk of imparting a sense of discomfort to the legs of a wearer.

In contrast, in the first embodiment according to the present invention, since the end portions 6SE are positioned farther to the inside in the transverse direction LT than the side portions 4LS and 5LS, the aforementioned problems do not occur. Moreover, since the surface area of the connecting sheet 6 can be decreased, material costs can be reduced. Note that the end portions 6SE are not necessarily required to extend in the transverse direction LT, but rather may also have a curved shape. In addition, only one of the end portions 6SE on the side of the front piece 4 and the end portions 6SE on the side of the back piece 5 may be positioned farther to the inside in the transverse direction LT than the side portions 4LS and 5LS.

Moreover, as was explained with reference to FIG. 6, since the connecting sheet 6 is attached to the front piece web W4 and the back piece web W5 that are suctioned and held, the connecting sheet 6 can be attached at the proper positions on the front piece web W4 and the back piece web W5.

Figure 8:
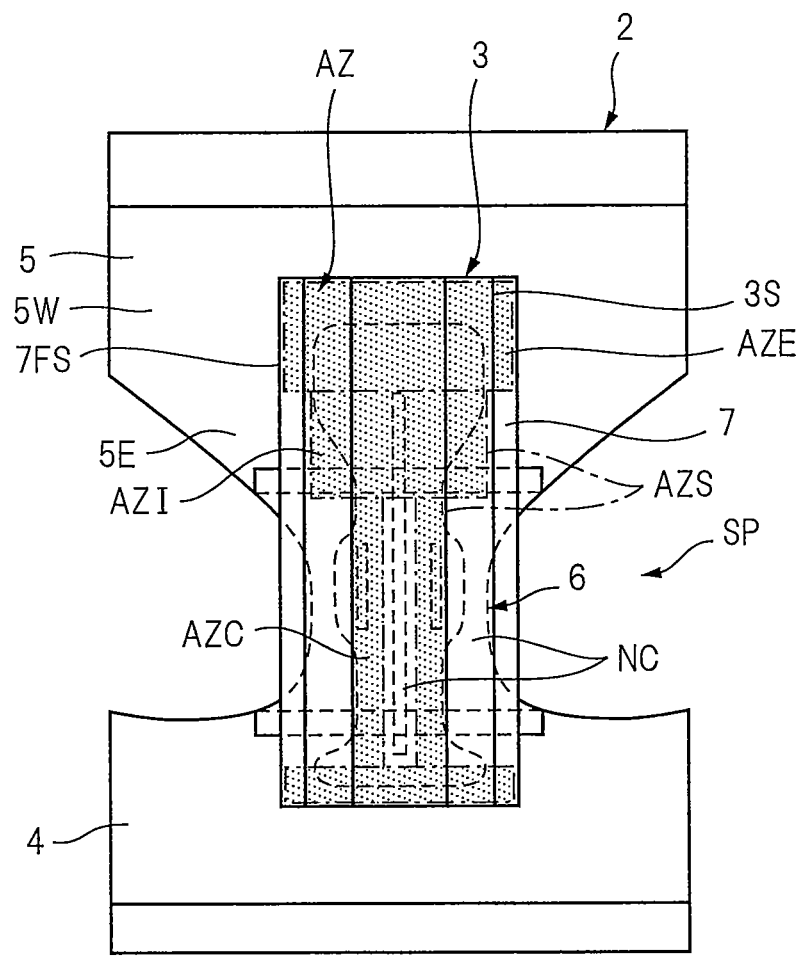
FIG. 8 is a drawing showing an adhesive application pattern.
Figure 8:
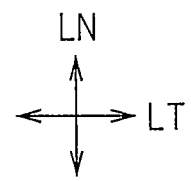

FIG. 8 shows an adhesive application pattern in step ST16.

As shown in FIG. 8, the width of an area AZ where an adhesive is applied varies along the longitudinal direction LN. Namely, the adhesive application area AZ has end areas AZE located on both ends in the longitudinal direction LN, a central area AZC located in the center in the longitudinal direction LN, and an intermediate area AZI located between the end area AZE and the central area AZC on the side of the back piece 5. Here, both end areas AZE and the intermediate area AZI do not overlap with the connecting piece 6, but rather the central area AZC overlaps with the connecting sheet 6.

The widths of both end areas AZE substantially coincide with the entire width of the inner body 3 and the leakage preventing members 7, and constitutes the largest width. This is to prevent the inner body 3 and the leakage preventing members 7 from separating from the front piece 4 and the back piece 5 and eliminate a sense of discomfort on the part of a wearer.

The width of the central area AZC is narrower than the width of the inner body 3 and constitutes the smallest width. In the first embodiment according to the present invention, the width of the central area AZC is about 90 mm.

The width of the intermediate area AZI is intermediate to the width of both end areas AZE and the central area AZC.

In this case, since adhesive is not applied to both sides in the transverse direction LT of the central area AZC and the intermediate area AZI, non-anchored areas NC are formed where the inner body 3 and the leakage preventing members 7 are not anchored to the outer body 2. The width of the non-anchored area NC around the central area AZC is larger than the width of the non-anchored area NC around the intermediate area AZI. Moreover, a non-anchored area NC is also formed in the center in the transverse direction of the central area AZC.

In this manner, a portion around the outer body 2, namely both edges 6S of the connecting sheet 6, and the inner body 3 are not mutually anchored between the front piece 4 and the back piece 5. Thus, the inner body 3 easily deforms corresponding to the physique of the wearer thereby enhancing adherence of the inner body 3.

The leakage preventing members 7 rise up by using as starting points edges AZS located on both sides in the transverse direction of the central area AZC and the intermediate area AZI. Thus, as a result of increasing the size of the non-anchored area NC around the central area AZC, the amount of the rise of the leakage preventing members 7 can be increased. In addition, adherence of the inner body 3 to the wearer can be enhanced.

In contrast, the non-anchored area NC around the intermediate area AZI is reduced in size, thereby suppressing rising of the leakage preventing members 7. As a result, excessive rising of the leakage preventing members 7 that causes them to cover the absorptive surface of the inner body 3 is prevented. In addition, if the intermediate area AZI is provided on the side of the back piece 5, namely the gluteal region of the wearer, the leakage preventing members 7 can be prevented from riding up into the seat of the gluteal region, thereby enhancing the sense of comfort.

Note that, in step ST16 (FIG. 5), the previously described pattern formation can be facilitated by applying adhesive in the machine direction MD of the inner body web W3 and the leakage preventing member webs W7.

Figure 9A:
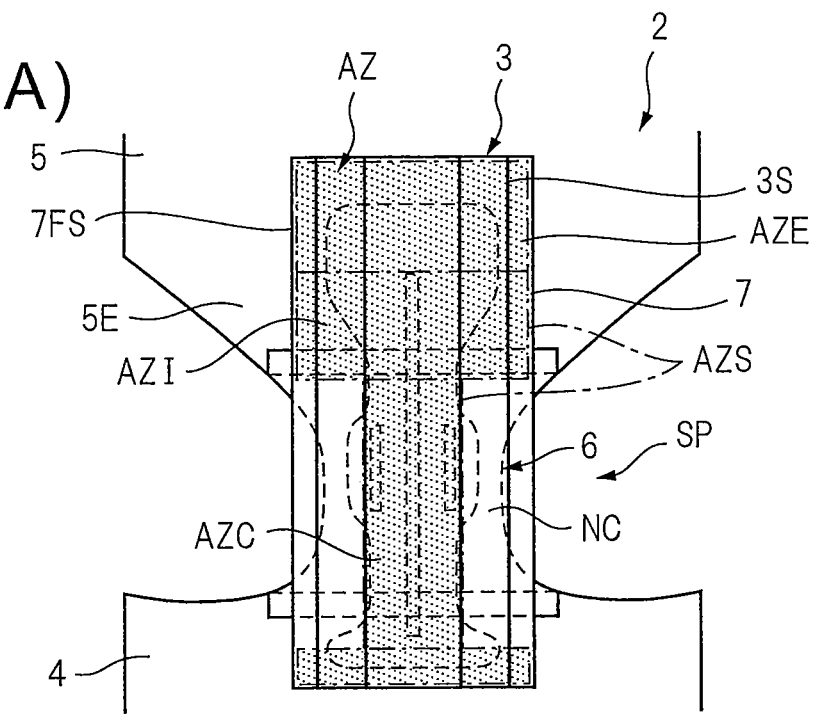
FIGS. 9(A) and 9(B) are drawings of other examples of adhesive application patterns.

Note that, as shown in FIG. 9(A), the width of the intermediate area AZI may be made to substantially coincide with the entire width of the inner body 3 and the leakage preventing members 7. In this case as well, excessive twisting of the leakage preventing members 7 can be prevented. Note that the non-anchored area NC in the center in the longitudinal direction LN is omitted in this example.

Figure 9B:
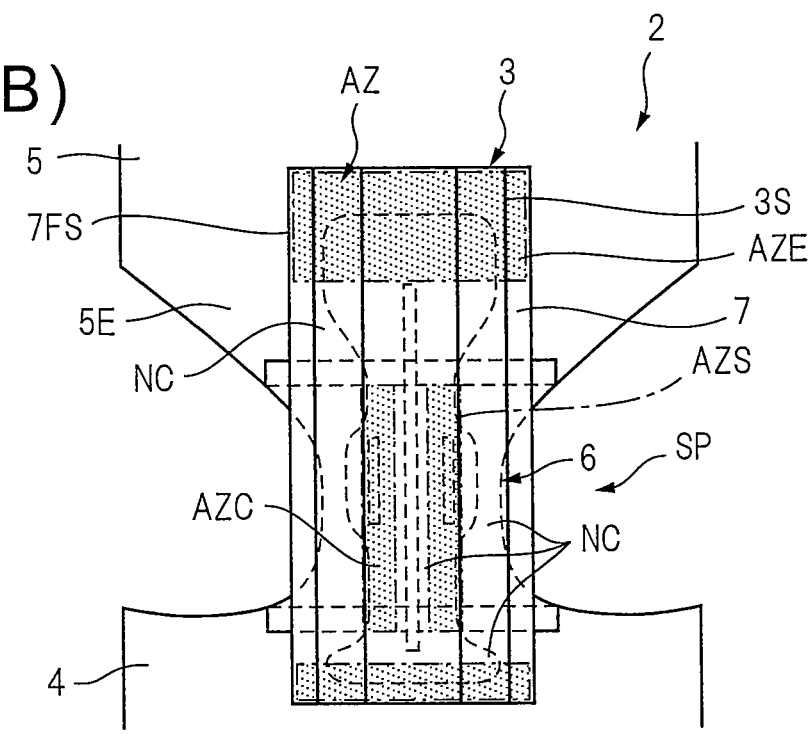

Alternatively, as shown in FIG. 9(B), non-anchored areas NC may also be provided adjacent to both end areas AZE. This being the case, wrinkling and twisting of the inner body 3 are suppressed. As a result, the sense of comfort is enhanced and stable absorptive performance of the inner body 3 is maintained.

Figure 10:
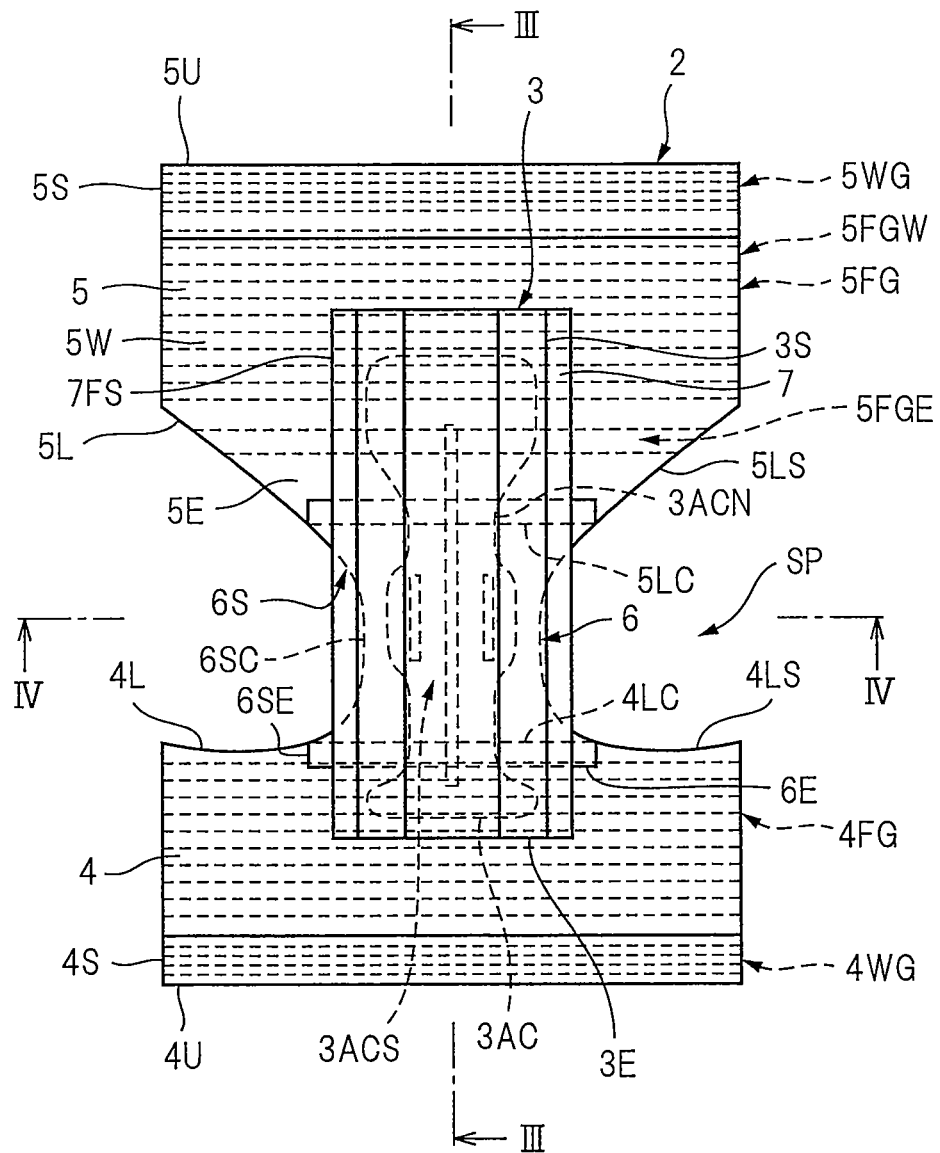
FIG. 10 is an open plan view for explaining a second embodiment according to the present invention.

FIG. 10 shows a second embodiment according to the present invention.

In this second embodiment according to the present invention, the elastic members 4LG and 5LG are omitted. Namely, the step for applying HMA for attaching the continuous elastic bodies W4LG and W5LG, and the step for attaching the continuous elastic bodies W4LG and W5LG to the top sheet webs W4T and W5T are omitted.

Figure 11:
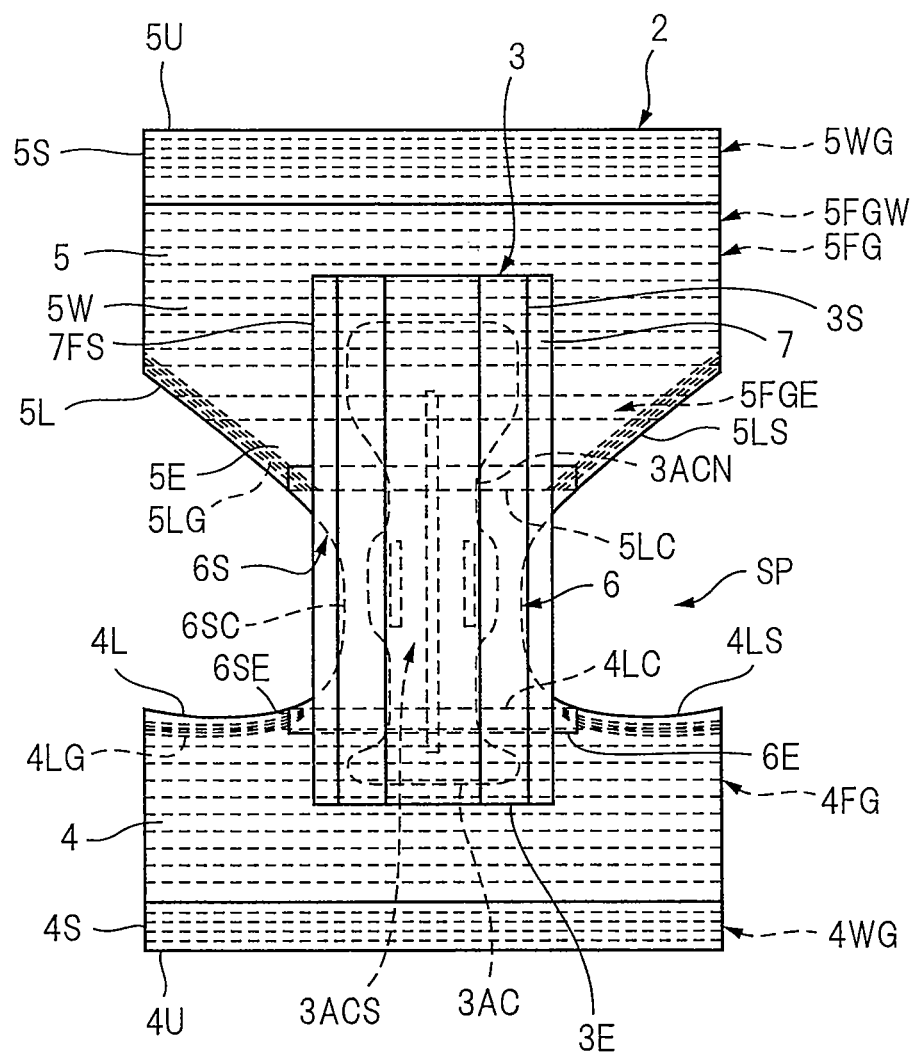
FIG. 11 is an open plan view for explaining a third embodiment according to the present invention.
Figure 11:
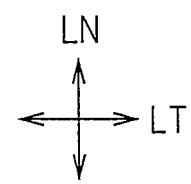

FIG. 11 shows a third embodiment according to the present invention.

In this third embodiment, the elastic members 4LG and 5LG are provided discontinuously. Namely, although the elastic members 4LG and 5LG are provided along the side portions 4LS and 5LS of the corresponding lower edges 4L and 5L, they are not provided along the central portions 4LC and 5LC.

Figure 12:
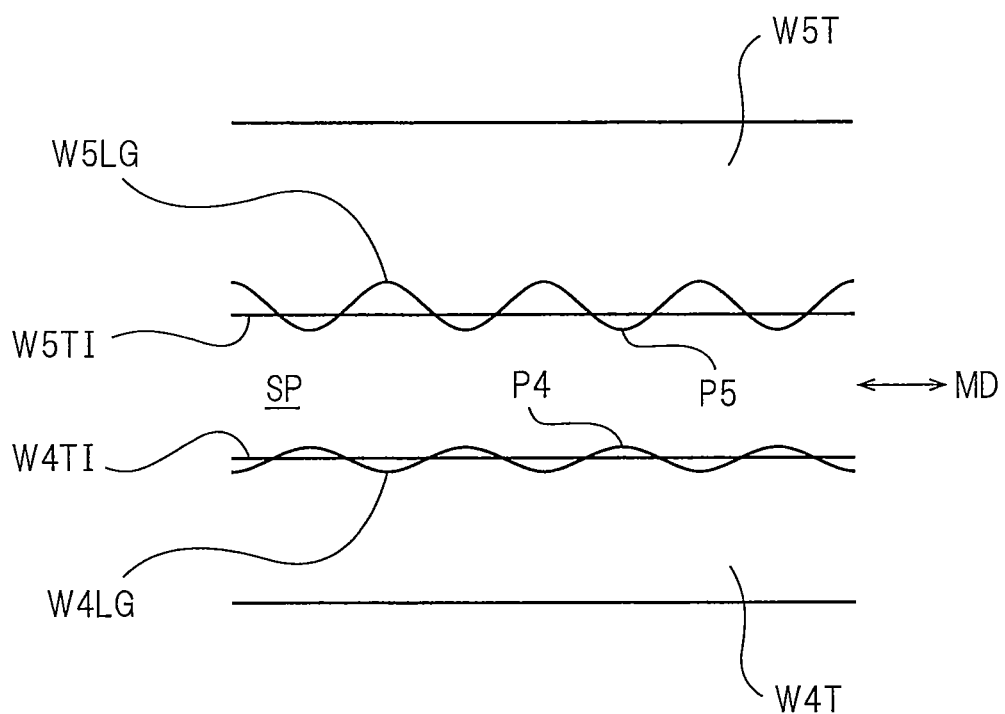
FIG. 12 is a partial schematic diagram for explaining a manufacturing method of a third embodiment according to the present invention.

In providing an explanation of the manufacturing method, the continuous elastic bodies W4LG and W5LG are supplied to the top sheet webs W4T and W5T and attached while oscillating in the same manner as the first embodiment. In this case, as shown in FIG. 12, the continuous elastic bodies W4LG and W5LG are oscillated across the inner edges of the corresponding top sheet webs W4T and W5T, namely edges W4T1 and W5T1 facing the spacing area SP, and as a result thereof, protrude from the top sheet webs W4T and W5T. Next, protruding portions P4 and P5 of the continuous elastic bodies W4LG and W5LG are cut and removed. Discontinuous elastic members 4LG and 5LG are formed in this manner.

Figure 13:
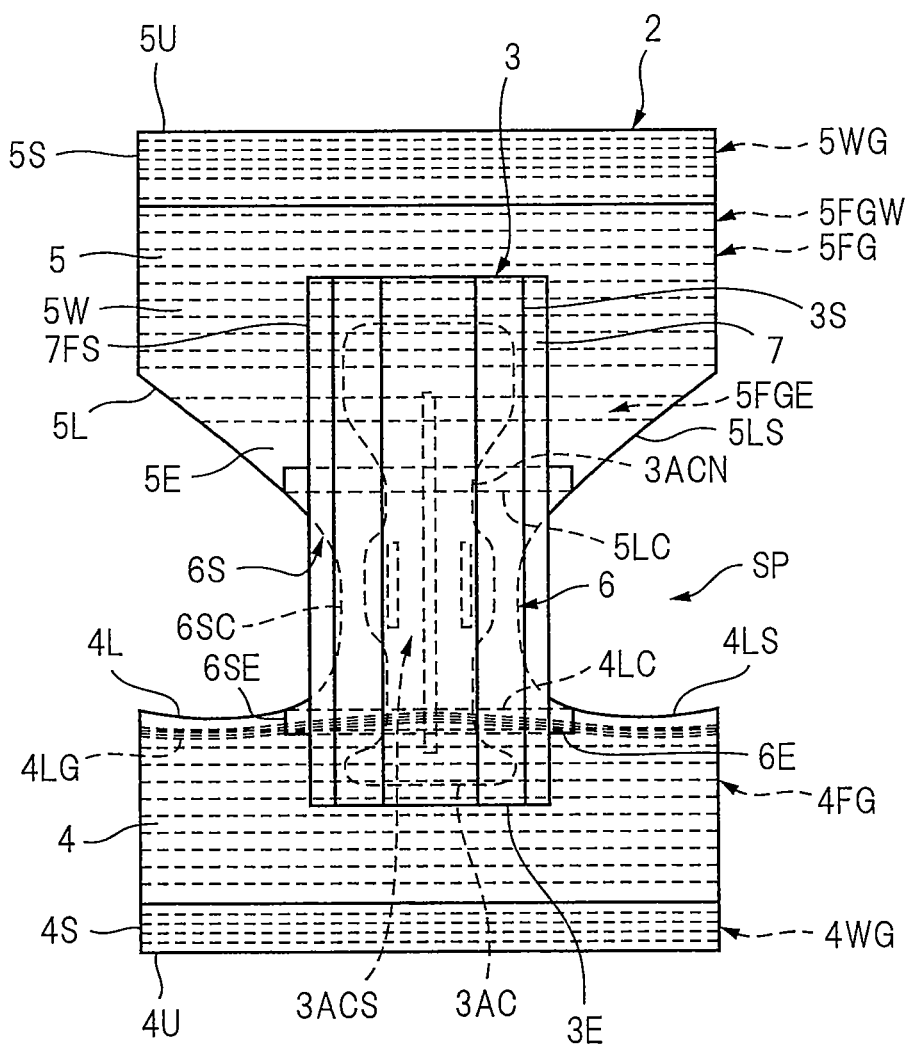
FIG. 13 is an open plan view for explaining a fourth embodiment according to the present invention.
Figure 13:
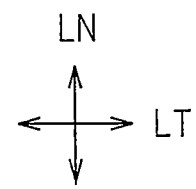

FIG. 13 shows a fourth embodiment according to the present invention.

In this fourth embodiment, the elastic member 4LG is provided with the elastic member 5LG is omitted. The elastic member 4LG may be continuous or discontinuous. However, if the elastic member 4LG of the front piece 4 is provided discontinuously, namely if the elastic member 4LG does not overlap with the inner body 3 or the connecting sheet 6, narrowing of the width of the inner body 3 on the abdominal side is suppressed. Thus, this is particularly preferable in the case the wearer is a male. On the other hand, in the case of providing the elastic member 4LG continuously, if the elastic member 4LG is provided adjacent to the urogenital region of women, adherence of the inner body 3 is enhanced. Alternatively, if the elastic member 4LG is provided to as to pass below the male genitalia, a space can be formed within the diaper 1, thereby enhancing comfort for male wearers. In addition, if the elastic members 4LG and 5LG are provided continuously, there is no longer a need to cut and remove the protruding continuous elastic body W5LG. In addition, since the elastic member 5LG overlaps with the inner body 3, the inner body 3 is further adhered to the wearer.

Figure 14:
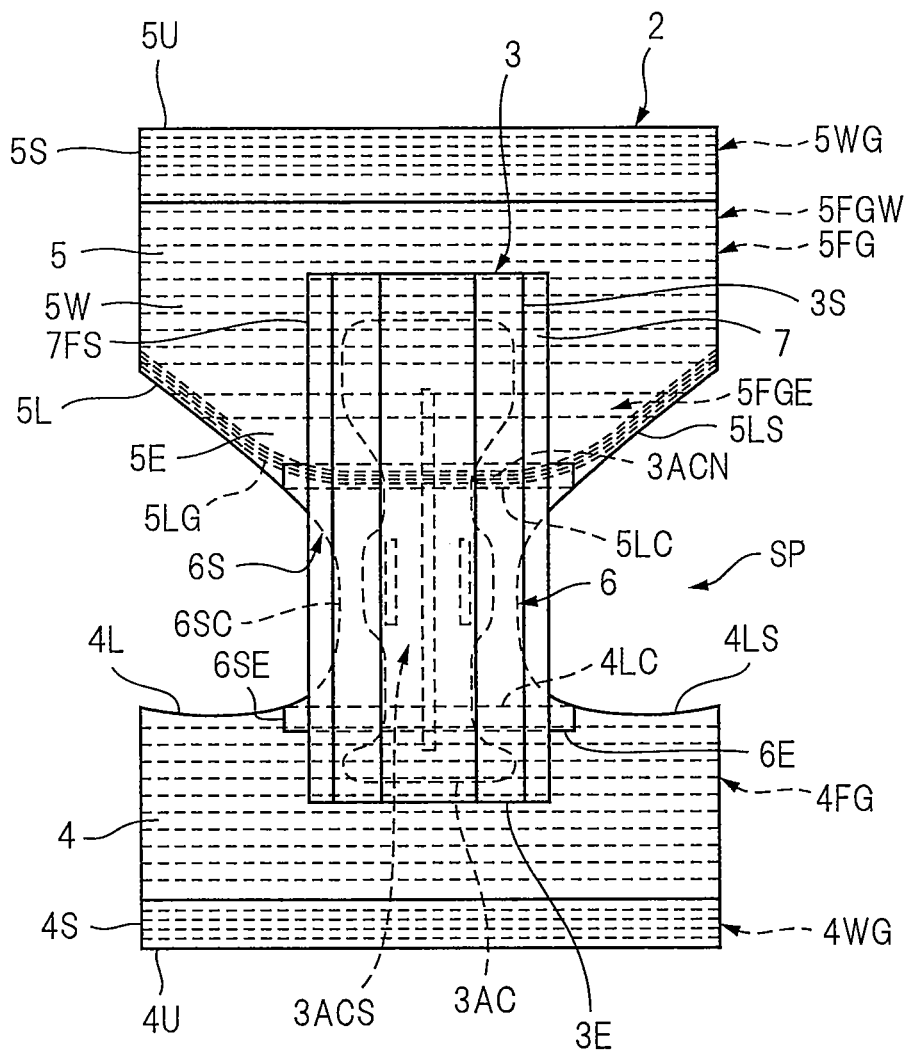
FIG. 14 is an open plan view for explaining a fifth embodiment according to the present invention.
Figure 14:
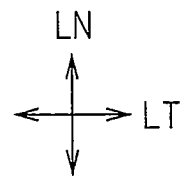

FIG. 14 shows a fifth embodiment according to the present invention.

In this fifth embodiment, the elastic member 5LG is provided while the elastic member 4LG is omitted.

Figure 15:
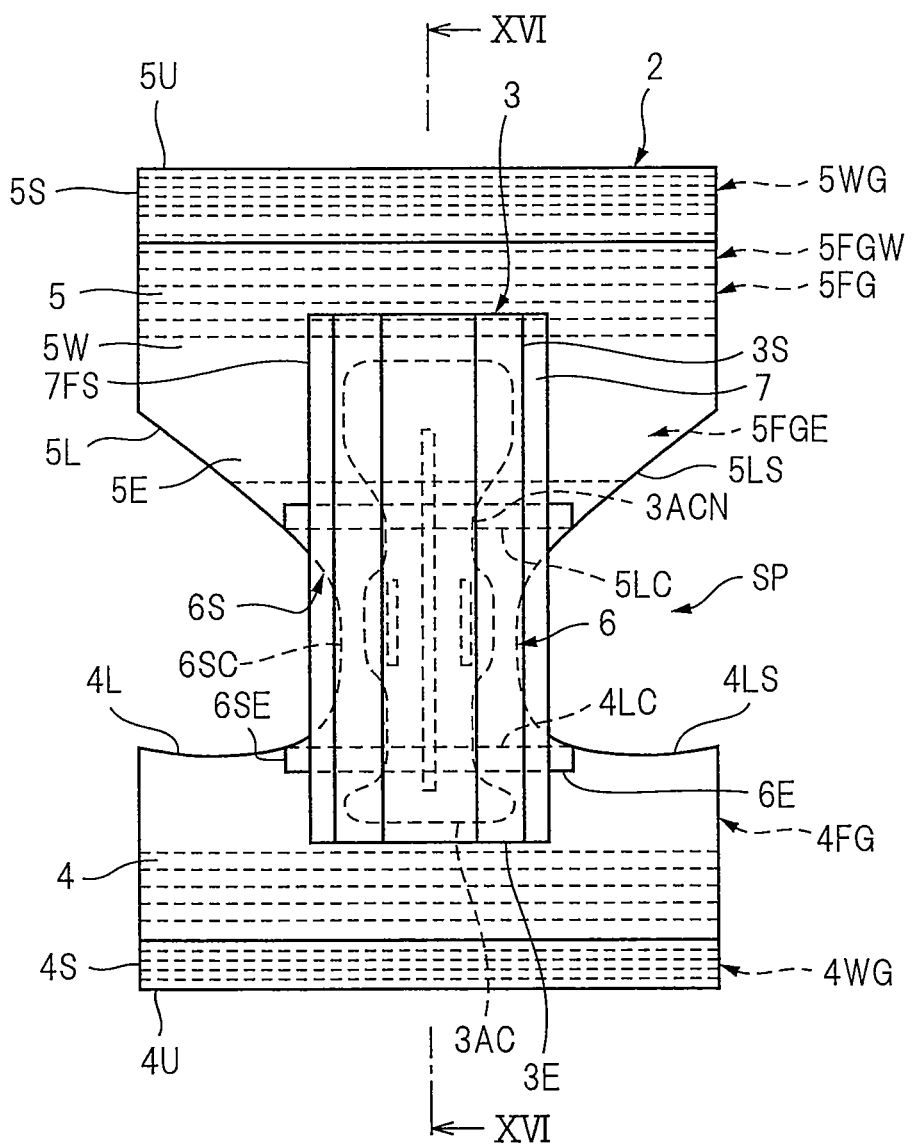
FIG. 15 is a drawing for explaining a sixth embodiment according to the present invention.
Figure 16:
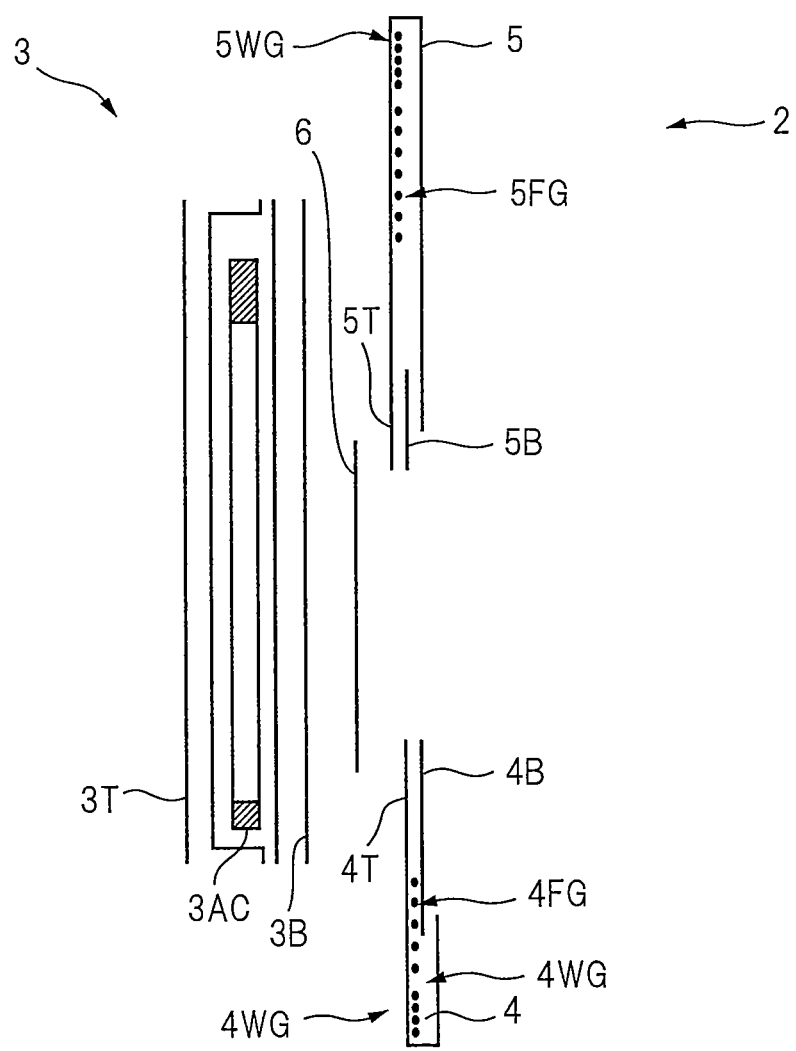
FIG. 16 is a cross-sectional view taken along line XVI-XVI of FIG. 15.
Figure 17:
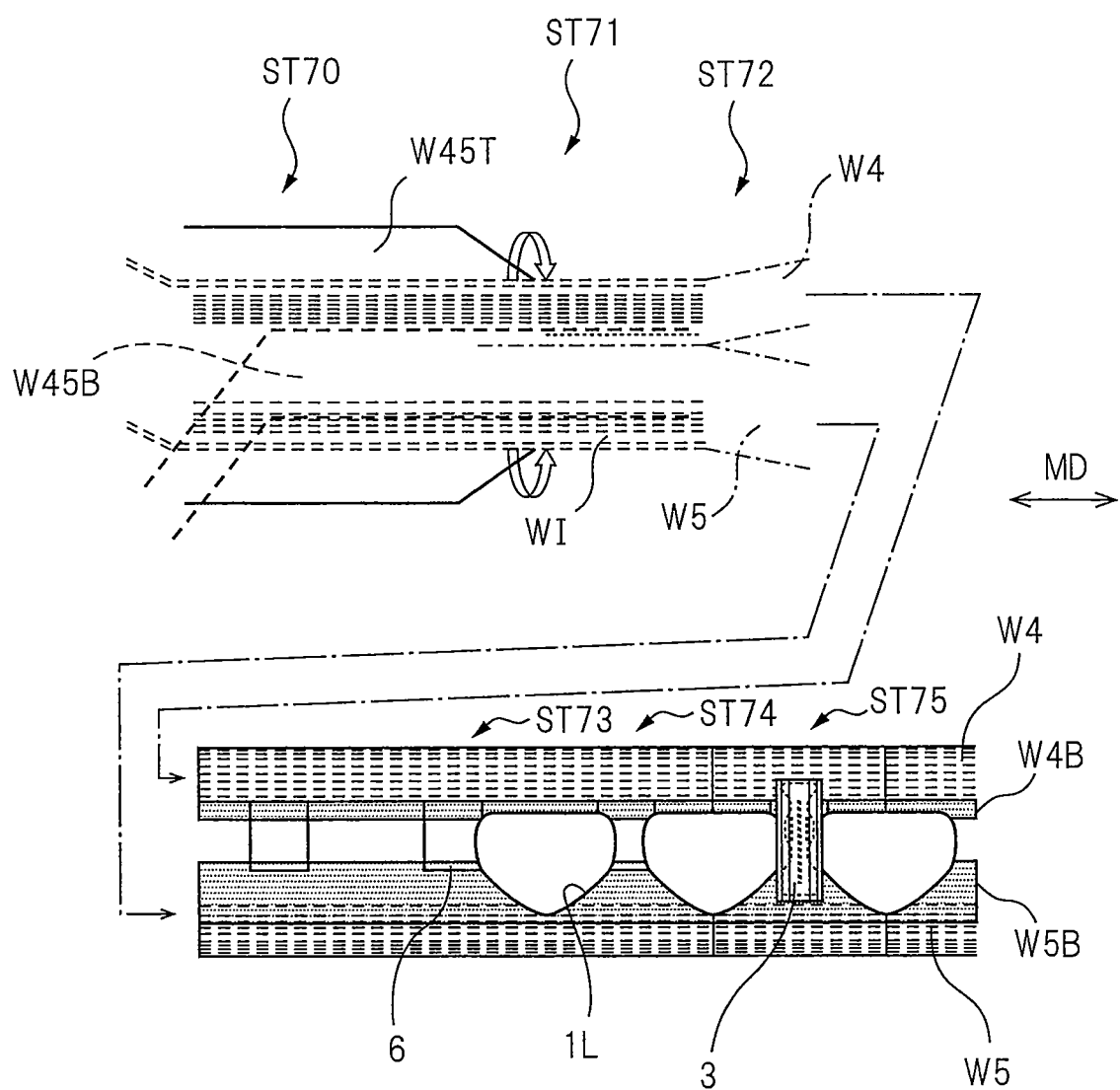
FIG. 17 is a schematic diagram for explaining a diaper manufacturing method of a sixth embodiment according to the present invention.

A sixth embodiment according to the present invention is indicated in FIGS. 15 to 17.

In this sixth embodiment, the top sheets 4T and 5T are formed from a non-stretchable non-woven fabric, while the back sheets 4B and 5B are formed from a stretchable sheet as shown in FIGS. 15 and 16.

A stretchable non-woven fabric containing, for example, stretchable thermoplastic fibers and elastomer fibers can be used for the stretchable sheet. In addition, polyolefin-based fibers in the manner of polypropylene or polyethylene fibers or polyester-based fibers in the manner of polyethylene terephthalate or polypropylene terephthalate fibers can be used for the thermoplastic fibers. In addition, urethane-based fibers such as polyurethane fibers, polystyrene-based fibers or rubber-based fibers and the like can be used for the elastomer fibers. Moreover, the stretchable non-woven fabric can be manufactured by a manufacturing method such as spunbonding or air-through bonding. Note that the stretchable non-woven fabric is used after having been gear-stretched to demonstrate stretching in the machine direction MD.

The back sheets 4B and 5B formed from a stretchable sheet in this manner provide elastic action between the side areas 1F and crotch area 10 of the diaper 1.

Note that the stretchable sheet may be provided continuously or discontinuously in the machine direction MD. In addition, the stretchable sheet can be provided in one or both of the front piece 4 and the back piece 5.

As shown in FIG. 17, the back sheet web W45B is affixed to the top sheet web W45T while stretched in the machine direction MD (ST70). Note that, at this time the continuous elastic bodies W4WG, W5WG, W4FG and W5FG to which adhesive has been applied are already supplied onto the top sheet web W45T.

Next, the top sheet web W45T is folded back at both side edges in the machine direction MD and overlapped with the back sheet web W45B (ST71). As a result, an integrated web WI is formed in which the back sheet web W45B and the continuous elastic bodies W4WG, W5WG, W4FG and W5FG are integrated into a single unit.

Next, the integrated web WI is divided into the front piece web W4 and the back piece web W5 (ST72). Next, the connecting sheet 6 is connected to the front piece web W4 and the back piece web W5 (ST73) to form the edges 1LE that define the leg holes 1L (ST74). Next, the inner body 3 is attached (ST75).

Note that, since the back sheet web W45B stretches in the machine direction MD and contracts in the cross-machine direction CD, a position controller is provided before each processing location so that the widths of the integrated web WI, front piece web W4 and back piece web W5 in the cross-machine direction CD are maintained at the proper values.

In the aforementioned sixth embodiment, the front piece 4 and the back piece 5 are formed from a mutually overlapping stretchable sheet and non-stretchable non-woven fabric. However, at least a portion of the front piece 4 or the back piece 5, such as a portion around the leg holes 1L, can also be formed from only a stretchable sheet. In this case, the portion formed only from the stretchable sheet is formed from one or a plurality of stretchable sheets. In the case of forming this portion from a stretchable non-woven fabric in the manner of a stretchable urethane spun-bond fabric, the basis weight of that portion is preferably 50 g/m² or more, and for example, 80 g/m². This being the case, stretchability of the front piece 4 or the back piece 5 is improved, or in other words, the maximum stretched dimension of the front piece 4 or the back piece 5 becomes larger or stretching occurs in the longitudinal direction LN of the diaper 1 (see FIG. 2). As a result, the front piece 4 or the back piece 5 closely fits the legs of the wearer around the leg holes 1L thereby resulting in greater comfort.

Figure 18:
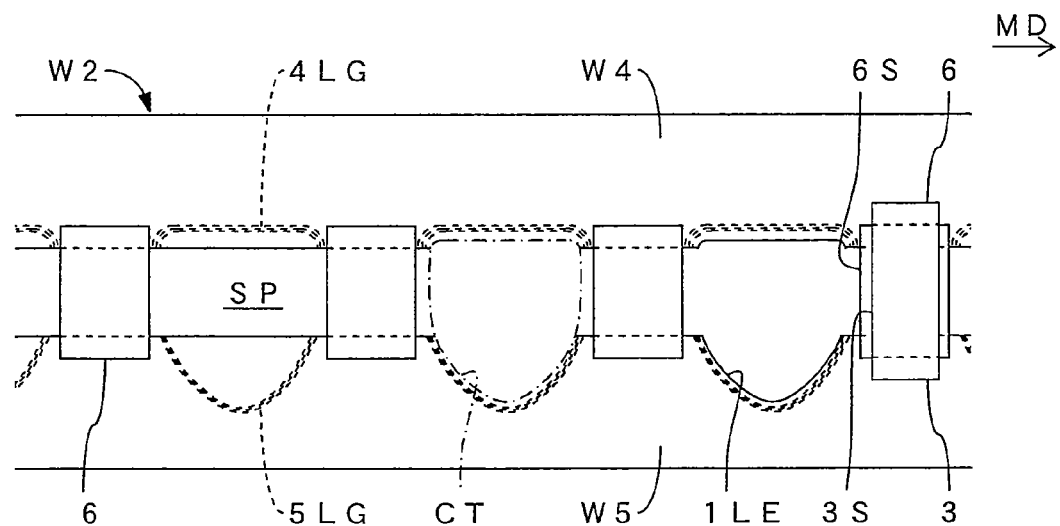
FIG. 18 is a drawing for explaining a seventh embodiment according to the present invention.

FIG. 18 shows a seventh embodiment according to the present invention.

In this seventh embodiment as well, the outer body web W2 provided with the connecting sheet 6 is cut along the cutting line CT to form the edges 1LE that define the leg holes 1L. In this case, the front piece web W4 and the back piece web W5 are cut, but the connecting sheet 6 is not cut. As a result, the connecting sheet 6 maintains a rectangular shape that is free of a narrow portion. As a result, since the front piece web W4 and the back piece web W5 are not cut together with the comparatively soft connecting sheet 6, the load on the cutting blade used in the cutting action can be reduced, thereby making it possible to extend the life of the cutting blade.

Next, the inner body 3 is attached to the outer body web W2 so as to overlap the connecting sheet 6. In this case, the entire side edges 6S of the connecting sheet 6 are positioned farther to the outside in the transverse direction LT than both side edges 3S of the outer body 3. This being the case, the effect of the inner body 3 being pulled up towards the side areas 1F of the diaper 1 (FIG. 1) can be enhanced.

Figure 19:
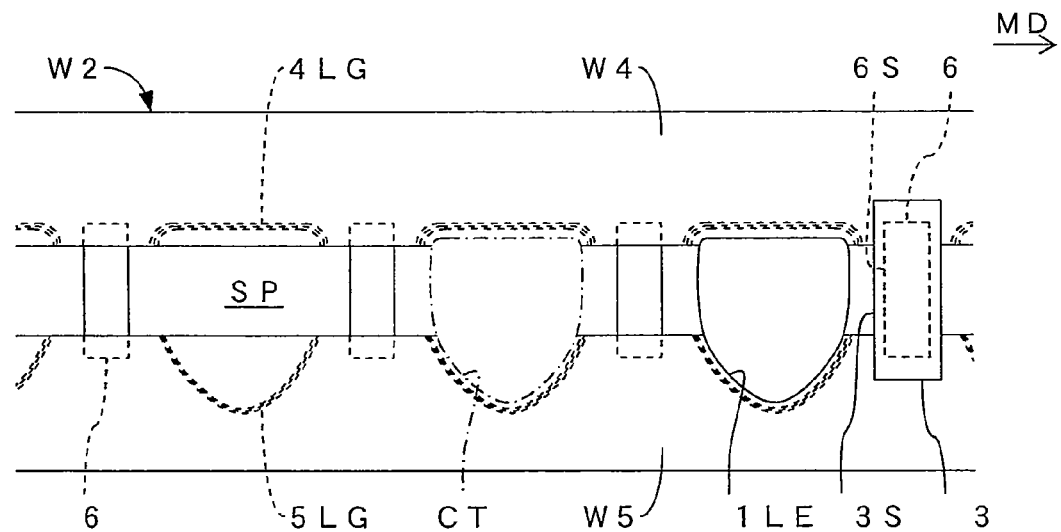
FIG. 19 is a drawing for explaining an eighth embodiment according to the present invention.

FIG. 19 shows an eighth embodiment according to the present invention.

In this eighth embodiment as well, the outer body web W2 provided with the connecting sheet 6 is cut along the cutting line CT to form the edges 1LE. In this case, similar to the case of FIG. 18, the front piece web W4 and the back piece web W5 are cut, but the connecting sheet 6 is not cut. Note that, in the example shown in FIG. 19, the areas around both ends of the connecting sheet 6 in the longitudinal direction LN are sandwiched between the top sheet web and the back sheet web of the front sheet web W4 and the back sheet web W5.

Next, the inner body 3 is attached to the outer body web W2 so as to overlap the connecting sheet 6. In this case, the entire side edges 6S of the connecting sheet 6 are positioned farther to the inside in the transverse direction LT than both side edges 3S of the inner body 3. This being the case, the range of movement of the legs of a wearer can be increased while maintaining favorable absorptive performance of the inner body 3, while at the same time material costs can be further reduced.

Figure 20:
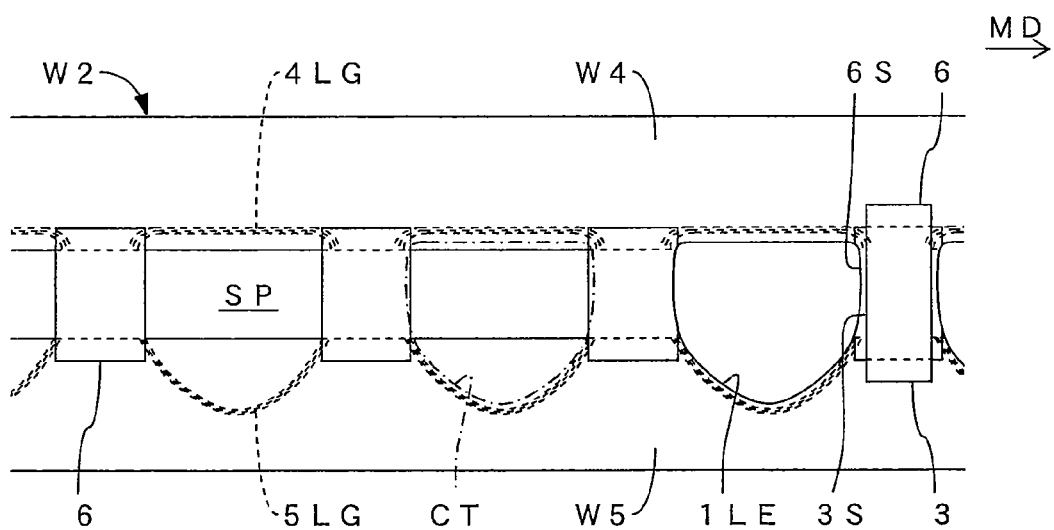
FIG. 20 is a drawing for explaining a ninth embodiment according to the present invention.

FIG. 20 shows a ninth embodiment according to the present invention.

In this ninth embodiment as well, the outer body web W2 provided with the connecting sheet 6 is cut along the cutting line CT to form the edges 1LE. In this case, the front piece web W4, the back piece web W5 and the connecting sheet 6 are cut in the same manner as the case of FIG. 5.

Next, the inner body 3 is attached to the outer body web W2 so as to overlap the connecting sheet 6. In this case, similar to the case of FIG. 18, the entire side edges 6S of the connecting sheet 6 are positioned farther to the outside in the transverse direction LT than both side edges 3S of the inner body 3. As a result, the effect of pulling up the inner body 3 is enhanced while enabling the leg holes 1L to be formed to a shape that fits the legs of the wearer.

Note that, in the embodiments described thus far, the front piece web W4 and the back piece web W5 are cut at the stage of cutting to form the edges 1LE. However, only one of the front piece web W4 and the back piece web W5 may be cut.

In addition, the connecting sheet 6 may also not be cut at the stage of cutting to form the edges 1LE as shown in FIG. 18, for example, or the connecting sheet may be cut as shown, for example, in FIG. 20.

Therefore, in conceptual terms, at the stage of cutting for forming the edges 1LE, the connecting sheet 6 is cut together with at least one of the front piece web W4 and the back piece web W5 so that both edges 6S in the transverse direction of the connecting sheet 6 are curved inward, or at least one of the front piece web W4 and the back piece web W5 is cut without cutting the connecting sheet 6.

Each of the previously described embodiments can also be mutually combined.

REFERENCE SIGNS LIST

1 Diaper
1C Crotch area
1F Side areas
1L Leg holes
2 Outer body
3 Inner body
4 Front piece 5 Back piece
6 Connecting sheet
7 Leakage preventing members
SP Spacing area

The invention claimed is:

1. A method of manufacturing an underpants-type absorbent article, which is provided with:
- an outer body, provided with a mutually separate front piece, back piece and connecting sheet, and wherein the front piece and the back piece are mutually joined at side areas and are mutually connected by the connecting sheet extending in the front-to-rear direction at the crotch area, and
- an inner body, containing an absorptive body and which is overlapped and anchored to the connecting sheet on the inside of the outer body, comprising, in turn:
- a transport step for transporting a continuous body of the front piece in the form of a front piece web and a continuous body of the back piece in the form of a back piece web in a machine direction while maintaining a spacing area in a cross-machine direction perpendicular to the machine direction,
- an outer body web forming step for forming a continuous body of the outer body in the form of an outer body web by attaching the connecting sheet to the front piece web and the back piece web at intervals in the machine direction so as to straddle the spacing area,
- an edge forming step for cutting the outer body web in order to form edges that define leg holes, and
- an attachment step for attaching the inner body to the outer body web,
- wherein, in the edge forming step, the connecting sheet is cut so that both edges in the transverse direction of the connecting sheet are inwardly curved, and thus at least a portion of both edges in a transverse direction of the connecting sheet are positioned closer to a centerline of the inner body than both edges in the transverse direction of the inner body in an area between the front piece and the back piece.

2. The method according to claim 1, wherein the front sheet web and the back sheet web are respectively provided with a mutually overlapping top sheet web and a back sheet web, and in the outer body web forming step, the areas around both ends of the connecting sheet in a longitudinal direction are respectively sandwiched between the top sheet web and back sheet web of the front piece web and between the top sheet web and back sheet web of the back piece web.

3. The method according to claim 1, further comprising a step for attaching elastic members, which provide an elastic action between the side areas and the crotch area, to the front piece web or the back piece web prior to the outer web forming step.

4. The method according to claim 3, wherein, in the edge forming step, the front piece web or the back piece web is cut so as to follow the elastic members.

5. The method according to claim 1, wherein, in the edge forming step, the outer body web is cut so that the edges that define the leg holes are smoothly curved and continuing.

6. The method according to claim 1, wherein, in the edge forming step, the connecting sheet is cut together with at least one of the front piece web and the back piece web so that both edges in the transverse direction of the connecting sheet curve inward, or at least one of the front piece web and the back piece web is cut without cutting the connecting sheet.

7. The method according to claim 1, wherein, in the attachment step, the inner body is attached to the outer body web so that non-anchored areas where the connecting sheet and the inner body are not mutually anchored, are formed around both ends in the transverse direction of the connecting sheet.

\* \* \* \* \*